United States Patent
Ye et al.

(10) Patent No.: US 10,196,359 B2
(45) Date of Patent: Feb. 5, 2019

(54) 2-ALKYLOXY BENZENE FORMYL ARYLAMINE COMPOUND AND PHARMACEUTICAL USE THEREOF

(71) Applicant: FUDAN UNIVERSITY, Shanghai (CN)

(72) Inventors: Deyong Ye, Shanghai (CN); Yali Li, Shanghai (CN); Lu Zhou, Shanghai (CN); Penghui Wang, Shanghai (CN); Yong Chu, Shanghai (CN); Haojun Gong, Shanghai (CN); Qi Huang, Shanghai (CN); Yan Chen, Shanghai (CN); Zhikuan Zhang, Shanghai (CN)

(73) Assignee: FUDAN UNIVERSITY, Shanghai (CN)

( * ) Notice: Subject to any disclaimer, the term of this patent is extended or adjusted under 35 U.S.C. 154(b) by 0 days.

(21) Appl. No.: 15/513,340

(22) PCT Filed: Jul. 24, 2015

(86) PCT No.: PCT/CN2015/085077
§ 371 (c)(1),
(2) Date: Mar. 22, 2017

(87) PCT Pub. No.: WO2016/029767
PCT Pub. Date: Mar. 3, 2006

(65) Prior Publication Data
US 2017/0253564 A1    Sep. 7, 2017

(30) Foreign Application Priority Data
Aug. 24, 2014   (CN) .......................... 2014 1 0419334

(51) Int. Cl.
*C07D 213/75*    (2006.01)
*A61K 31/4406*   (2006.01)
*A61K 31/505*    (2006.01)
*A61K 31/5377*   (2006.01)
*C07D 239/42*    (2006.01)

(52) U.S. Cl.
CPC ........ *C07D 213/75* (2013.01); *A61K 31/4406* (2013.01); *A61K 31/505* (2013.01); *A61K 31/5377* (2013.01); *C07D 239/42* (2013.01)

(58) Field of Classification Search
None
See application file for complete search history.

(56) References Cited

FOREIGN PATENT DOCUMENTS

WO    WO-0177077 A1 * 10/2001 ........... C07C 311/05

OTHER PUBLICATIONS

Ponci et al, Chemical Abstracts 59:41585, Abstract of Farmaco, Edizione Scientifica, 18(4), pp. 288-304 (Year: 1963).*

* cited by examiner

*Primary Examiner* — Zinna Northington Davis
(74) *Attorney, Agent, or Firm* — Ware, Fressola, Maguire & Barber LLP

(57) ABSTRACT

2-alkoxy benzene formyl arylamine compounds and their pharmaceutical salts are disclosed. The compounds can act as sphingomyelin synthase (SMS) inhibitors to treat diseases caused by abnormal increasing of sphingomyelin (SM). The pharmaceutically acceptable salts and pharmaceutical compositions of the compounds are used as active ingredients in drugs which can prevent and cure diseases caused by SM level abnormal increase. These diseases include atherosclerosis, fatty liver, obesity, type diabetes, and other metabolic syndromes.

5 Claims, No Drawings

2-ALKYLOXY BENZENE FORMYL ARYLAMINE COMPOUND AND PHARMACEUTICAL USE THEREOF

TECHNICAL FIELD

The present invention belongs to the field of medicinal chemistry, which is about the 2-alkoxy benzene formyl arylamine compounds and their pharmaceutical uses, especially the 2-alkoxy benzene formyl arylamine compounds and their uses in preparing sphingomyelin synthase inhibitors, and uses in prevention or treatment of atherosclerosis, fatty liver, obesity, type II diabetes, and other metabolic syndromes.

BACKGROUND TECHNOLOGY

As reported, with the development of economic society and the aging of the population, morbidity and mortality of cardiovascular diseases have increased significantly in recent years, ranking the second place in total mortality, just behind cancer, becoming the main diseases that threaten human health. Studies showed that atherosclerosis (AS) is one of the main pathological basis of many cardiovascular diseases, making anti-atherosclerosis drugs a hot field of drug development. The study also conveyed that atherosclerosis is manifested as the yellow substances such as cholesterol and lipid in the endarterium, leading to thrombogenesis and blood supply insufficiency. Although its molecular pathology is not entirely understood, it is widely accepted that, among many factors, dyslipidemia is the most important factor in causing atherogenesis and that the formation of atheromas and arteriosclerosis are closely related to the abnormal expression of the lipid component.

Generally speaking, dyslipidemia refers to higher lipid level in plasma and higher blood viscosity caused by lipid metabolism or transfer anomaly, and blood viscosity increase which mainly characterized by an increase of low-density lipoprotein (LDL) and very low-density lipoprotein (VLDL) and a decrease of high-density lipoprotein (HDL). Therefore, reduce LDL and/or increase HDL can play a role in regulating blood lipids and hence plasma lipids regulator can function as the main clinically used drug for anti-atherosclerosis.

The plasma lipids regulator commonly used in clinic are mainly statins, fibrates, bile acid binding resins, nicotinic acid and so on. Among them, the statins take effect through inhibiting 3-hydroxy-3-methyl-glutaryl coenzyme A reductase (HMG CoA reductase), the key enzyme of cholesterol biosynthetic process, to reduce plasma LDL level, thus can reduce the morbidity of coronary heart diseases (Linsel-Nitschke P, Tall A R. *Nat. Rev. Drug. Discov,* 2005, 4, 193-206). However, studies also show that after using pravastatin and atorvastatin to treat patients with coronary diseases, though LDL cholesterol level can be reduced in varying degrees, these patients still have a high incidence rate of cardiovascular diseases (Cannon C P, Braunwald E, et al. *N Engl J Med,* 2004, 350: 1495-1504). Thus, the treatment effect of simply reducing LDL cholesterol is limited. Furthermore, some studies have shown that statins have other serious side effects such as rhabdomyolysis.

With further researches, studies have proposed many potential anti-atherosclerosis drug targets, including sphingomyelin synthase inhibitors, PPAR agonists, cholesteryl ester transfer protein (CETP) inhibitors, apolipoprotein infusion, liver X receptor agonists and phospholipid transfer protein (PLTP) inhibitors. Among them, sphingomyelin (SM) and related metabolic enzymes can change lipoprotein levels while conducting a series of cell-mediated process, which suggested that they play important roles in the development of the atherogenesis.

Studies have shown that SM can induce AS in various pathways, including (1) inhibiting lipolysis of triglyceride (TG) (Park T S, Panek R L, et al. *Atherosclerosis.* 2006, 189(2):264-72.); (2) delay the clearance of atherogenic remnant lipoprotein (Schlitt A, Hojjati M R, et al. *J Lipid Res.* 2005, 46(2):196-200.); (3) affecting HDL-mediated cholesterol reverse transport, causing removal obstacles of cholesterol (Sano O, Kobayashi A, et al. *J Lipid Res.* 2007, 48(11):2377-84; Marmillot P, Patel S, et al. *Metabolism.* 2007, 56(2):251-9.); (4) ceramide and products of SM synthesis or degradation are cell regulators which can affect cell proliferation, activation and apoptosis and hence affect the atherosclerotic plaque growth and stability (Park, T.-S.; Panek, R. L.; et al. *Circulation.* 2004, 110, 3465-3471.); (5) LDL enriched in SM has strong cohesion and adhesion power which can make macrophages easy to aggregate on arterial wall to form foam cells thus promote atherogenesis (Fan Y, Shi S, et al. *Arterioscler Thromb Vasc Biol,* 2010, 30:2114-20.).

Epidemiological surveys also show that: there is an independent correlation between human SM level and AS, and that the plasma concentration of SM is an independent risk factor to AS, thus it is of indicative meaning in evaluating AS development (Jiang, X.-C.; Paultre, F.; et al. *Arterioscler. Thromb. Vasc. Biol.* 2000, 20, 2614-2618; Zhiqiang Li; Maria J. Basterr; et al. *Biochimica et Biophysica Acta.* 2005, 1735, 130-134.); animal studies have shown that inhibiting de novo biosynthesis of SM can efficiently reduce plasma cholesterol and triglyceride levels and increase the HDL-cholesterol, thereby preventing further lesion of AS (Park, T.-S.; Panek, R. L.; et al. *Circulation.* 2004, 110, 3465-3471.); therefore, decrease of plasma SM or inhibition of SM synthesis are believed to retard or even block athegogenesis.

Studies also show that sphingomyelin synthase (SMS) is the key enzyme of the last step of SM de novo biosynthesis, which can catalyze ceramide and phosphatidylcholine (PC) to synthesis SM. Further studies find that SMS can directly regulate SM level, and that SMS overexpression is a common phenomenon in atherosclerotic pathological-changed tissue, making it to be one of the key indicators of atherosclerosis (Xian-cheng Jiang; Furcy Paultre; et al. *Arterioscler. Thromb. Vasc Biol.* 2000, 20, 2614-2618 Zhiqiang Li; Tiruneh K. et al. *Biochimica et Biophysica Acta,* 2007, 1771, 1186-1194.). In the animal experiments, atherosclerotic plaques in arcus aortae of SMS2 and apoE double-gene knockout mice are dramatically reduced, SM and other lipids in brachiocephalic artery are obviously decreased, while does not influence their normal physiology function (Fan Y, Shi S, et al. *Arterioscler. Thromb. Vasc Biol,* 2010, 30:2114-20.), which insinuates that the SMS catalytic synthesis of SM is at the last step of SM biosynthesis cycle and may cause relatively slighter potential adverse effects when inhibited. With all the evidence above, it is believed that reduce SM level through inhibiting SMS is a new method to treat atherosclerosis. SMS has potential advantages as an anti-atherosclerosis target. Thus SMS inhibitors can make a novel medication for AS.

Furthermore, some studies have found that SMS2 deficiency can prevent obesity and insulin resistance caused by high-fat diets; meanwhile, it is difficult to observe significant mature fatty plaques in the livers of SMS2 knock-out mice, suggesting that SMS2 can take part in formation of liver fatty plaques and can induce obesity and type II diabetes (Susumu Mitsutake, Kota Zama, et al. *Journal of Biological Chemistry.* 2011, 286(32), 28544-28555). Plasma SM decrease caused by SMS2 deficiency can improve animal tissue and physical insulin sensibility (Li Z, Zhang H, et al. *Mol. Cell. Biol.* 2011, 31(20): 4205-4218). Therefore, SMS small-molecule inhibitors can prevent and treat obesity, fatty liver, type II diabetes, and other metabolic syndromes.

D609 is one of the reported SMS inhibitors (Aimin Meng; Chiara Luberto; et al. *Experimental Cell Research,* 2004, 292, 385-392.), having a weak inhibitory activity of $IC_{50}=375$ μM along with an highly unstable xanthate structure (Bai, A. et al. *J. Pharmacol. Exp. Ther.* 2004, 309, 1051-1059), thus has a short half-life time; It is reported that with the method of homology modeling, a hSMS1 3D-protein structure model was firstly built (Zhang Ya; Lin Fu; et al. *Chin. J. Chem.* 2011, 29, 2421-2429), with which the substrate binding site of SMS was determined and varified through biological experiments (Calvin Yeang; Shweta Varshney; et al. *Biochimica et Biophysica Acta,* 2008, 1781, 610-617.). Furthermore, based on this 3D-protein model and the varified enzyme-substrate binding site, a new compound D2 was found as an SMS inhibitor (Xiaodong Deng, Fu Lin, et al. *European Journal of Medicinal Chemistry,* 2014, 73, 1-7). Compared with D609, D2 has a higher SMS2 inhibitory activity, with $IC_{50}=13.5$ μM in in vitro trials. However, it still has some drawbacks: the activity which is not good enough; the existence of potential toxic cyano group; and poor physical and chemical properties such as solvability and stability.

SUMMARY OF THE INVENTION

The present invention aims to conquer the drawbacks and defects of existing technology and shows 2-alkoxy benzene formyl arylamines and their pharmaceutical use, expressly concerned with 2-alkoxy benzene formyl arylamines and their uses in preparing SMS inhibitors and drugs used to prevent and treat atherosclerosis, fatty liver, obesity, and type II diabetes.

The first aim of the present invention is to provide 2-alkoxy benzene formyl arylamines compounds and their pharmaceutically acceptable salts. The 2-alkoxy benzene formyl arylamines are free alkalis and salts of compounds with the structure of scheme I.

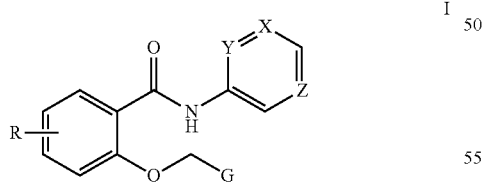

I

In the scheme I, X, Y and Z represent a carbon atom or a nitric atom, but X, Y and Z can not be carbon atom at the same time; G represents phenyl group, substituted phenyl groups or naphthyl group; when Y and X, or Y and Z are both carbon atoms, G will be chosen from phenyl group and naphthyl group; particularly, when G is substituted phenyl groups, substituent groups are one or two of halogen groups, nitro group, nitrile group, trifluoromethoxy group, carboxyl groups, ester groups, benzyloxy group, alkyl and alkoxy groups which contain one to seven carbon atoms; R represents hydrogen group, halogen groups, nitryl group or alkoxy groups which contain one to four carbon atoms.

Furthermore, when G is substituted phenyl groups, substituent groups are one or two of o-F, m-F, p-F, o-Cl, m-Cl, p-Cl, o-Br, m-Br, p-Br, o-$NO_2$, m-$NO_2$, p-$NO_2$, o-CN, m-CN, p-CN, o-$OCF_3$, m-$OCF_3$, p-$OCF_3$, o-COOH, m-COOH, p-COOH, o-COOEt, m-COOEt, p-COOEt, o-OBn, m-OBn, p-OBn, o-$OCH_2CO_2C_2H_5$, m-$OCH_2CO_2C_2H_5$, o-$OCH_2COOH$, m-$OCH_2COOH$, alkyl and alkoxy groups which contain one to seven carbon atoms.

That can be further described as scheme I-1 to scheme I-60:

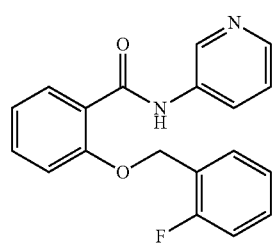

Scheme I-1

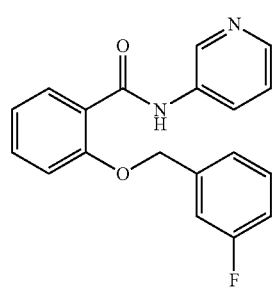

Scheme I-2

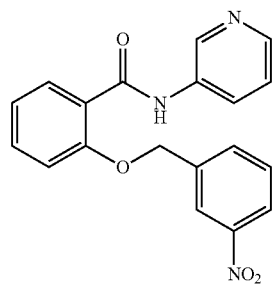

Scheme I-3

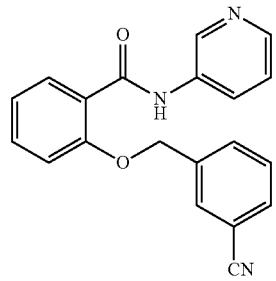

Scheme I-4

Scheme I-5
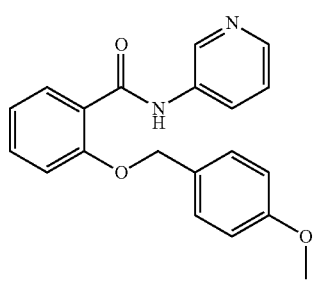
Scheme I-6
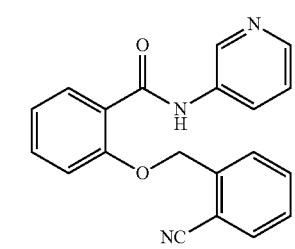
Scheme I-7
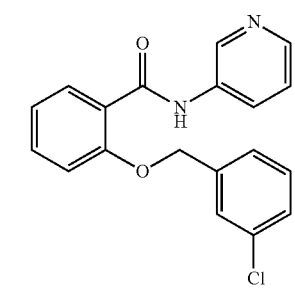
Scheme I-8
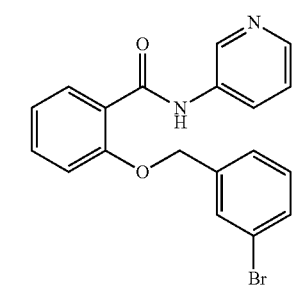
Scheme I-9
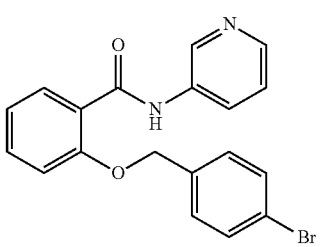
Scheme I-10
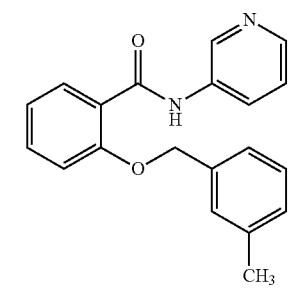
Scheme I-11
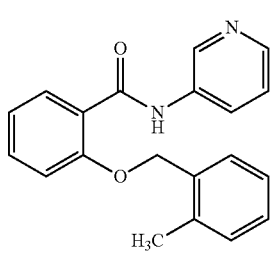
Scheme I-12
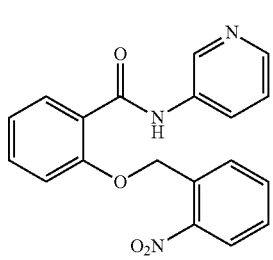
Scheme I-13
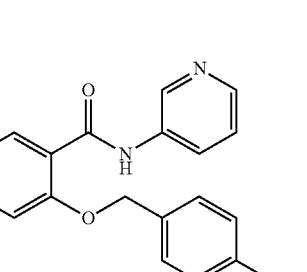
Scheme I-14
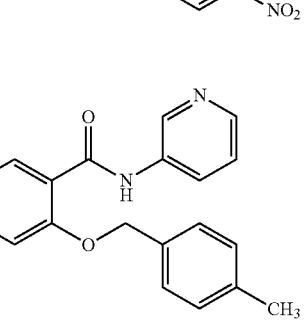
Scheme I-15
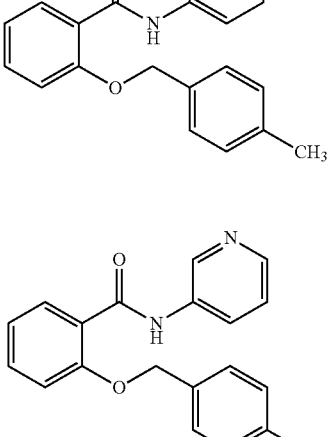
Scheme I-16
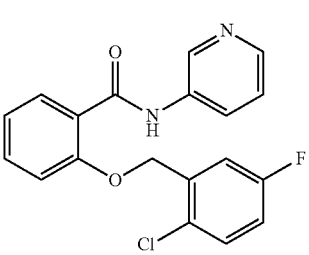

Scheme I-17
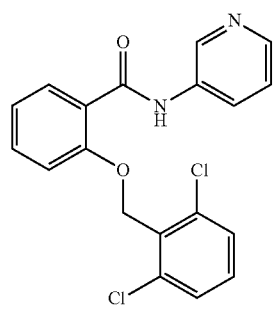
Scheme I-18
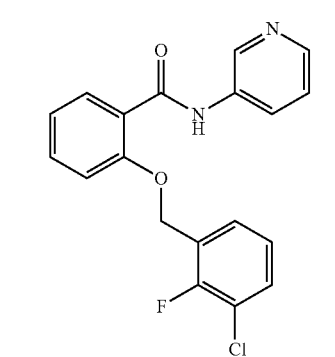
Scheme I-19
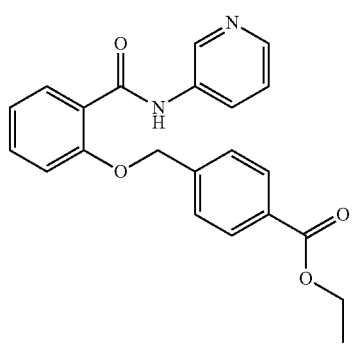
Scheme I-20
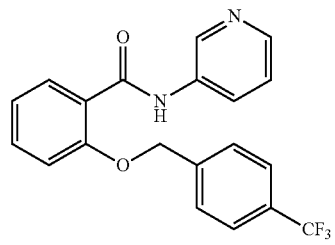
Scheme I-21
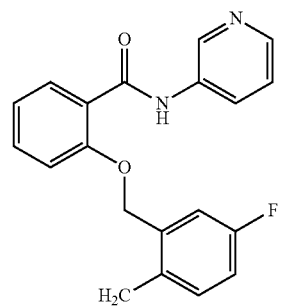
Scheme I-22
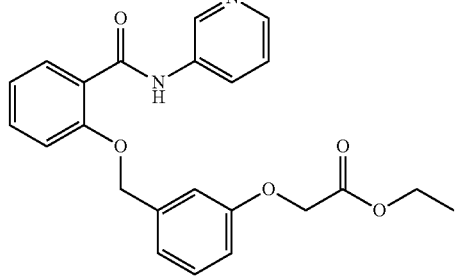
Scheme I-23
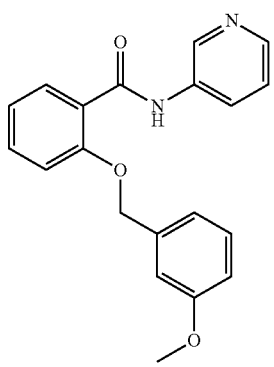
Scheme I-24
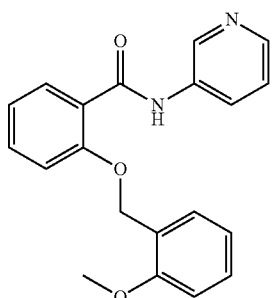
Scheme I-25
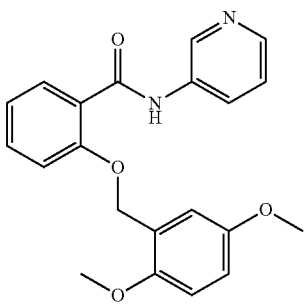
Scheme I-26
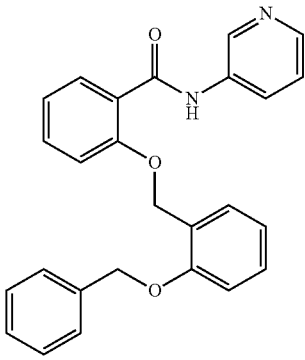

Scheme I-27
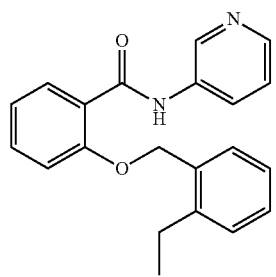
Scheme I-28
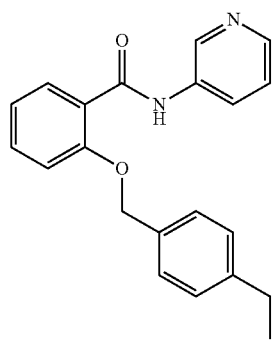
Scheme I-29
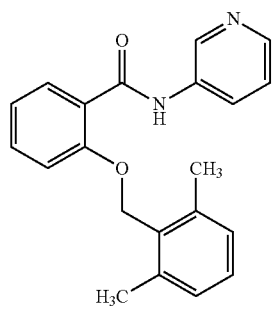
Scheme I-30
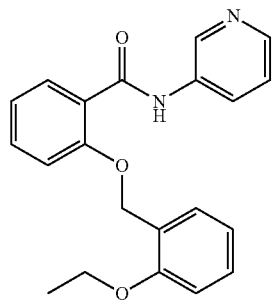
Scheme I-31
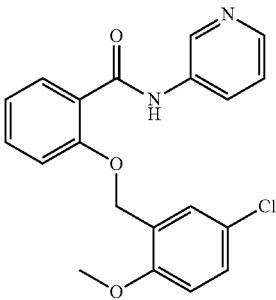
Scheme I-32
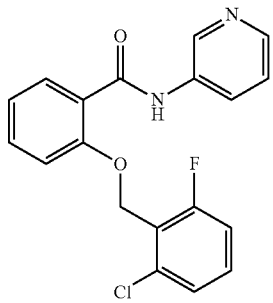
Scheme I-33
Scheme I-34
Scheme I-35
Scheme I-36

Scheme I-37
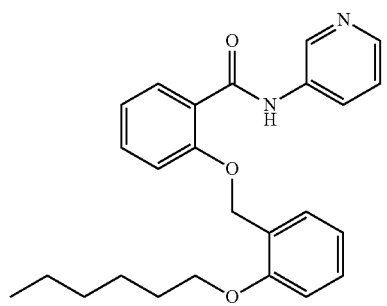
Scheme I-38
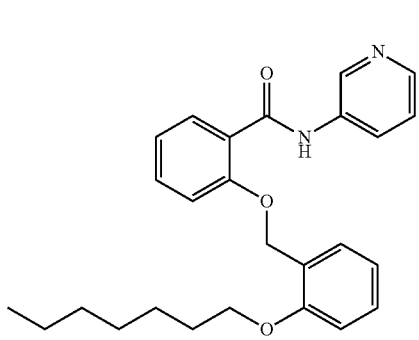
Scheme I-39
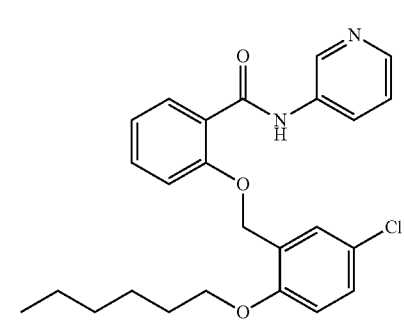
Scheme I-40
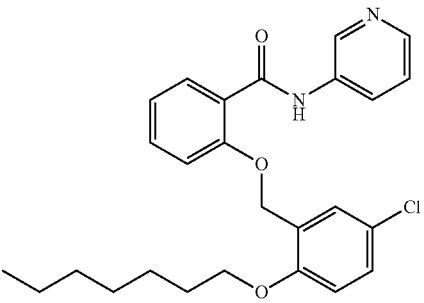
Scheme I-41
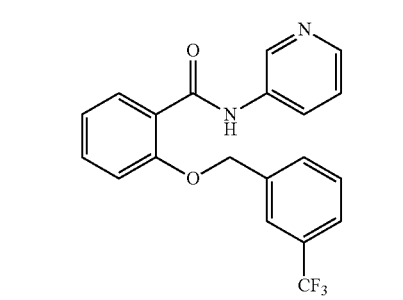
Scheme I-42
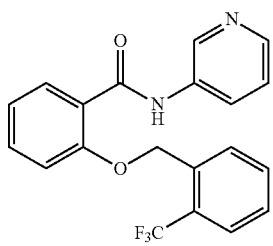
Scheme I-43
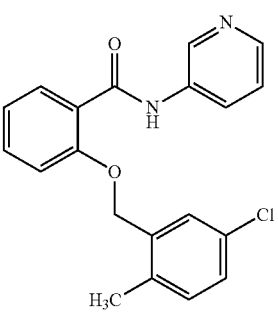
Scheme I-44
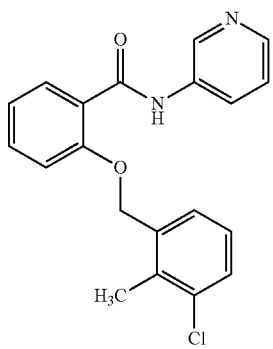
Scheme I-45
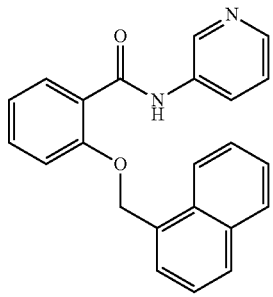
Scheme I-46
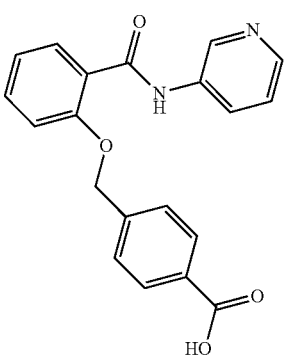

Scheme I-47
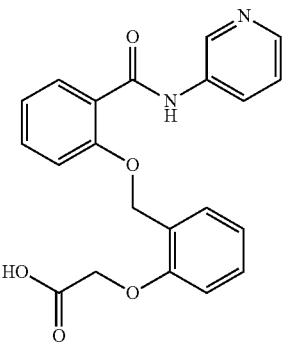
Scheme I-48
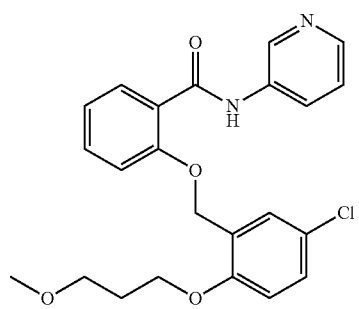
Scheme I-49
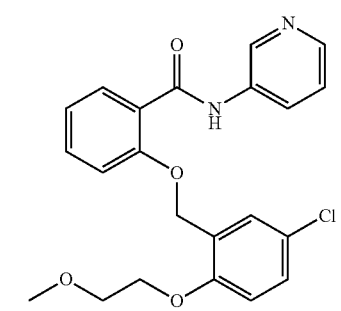
Scheme I-50
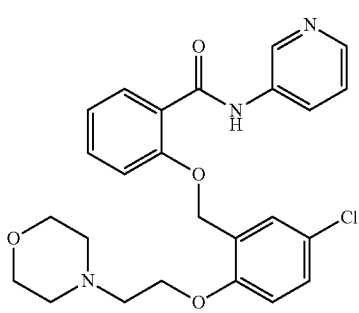
Scheme I-51
Scheme I-52
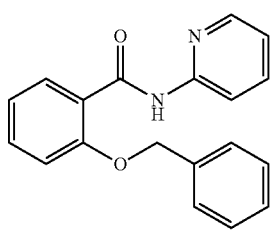
Scheme I-53
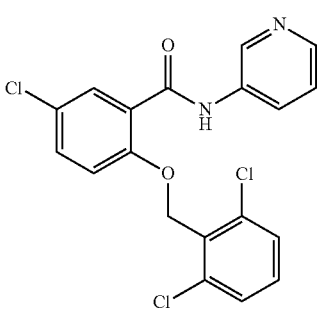
Scheme I-54
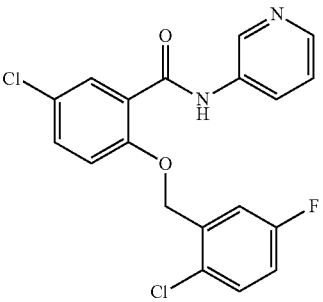
Scheme I-55
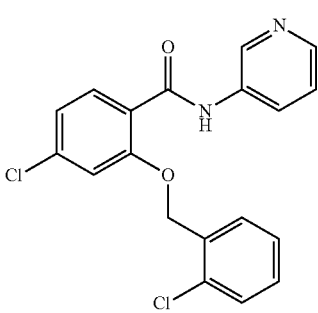
Scheme I-56

Scheme I-57

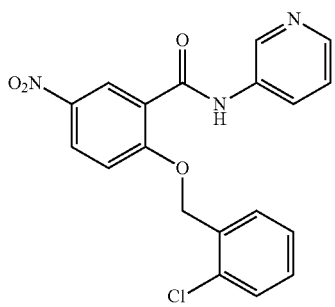

Scheme I-58

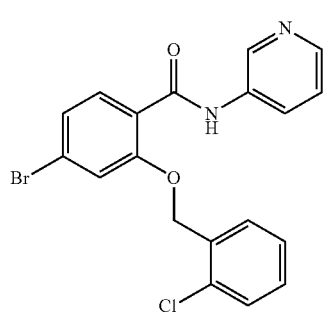

Scheme I-59

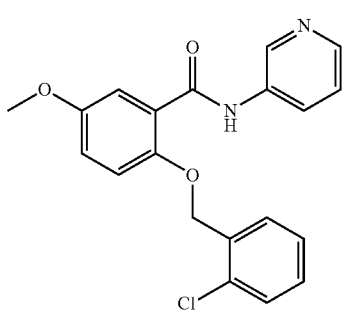

Scheme I-60

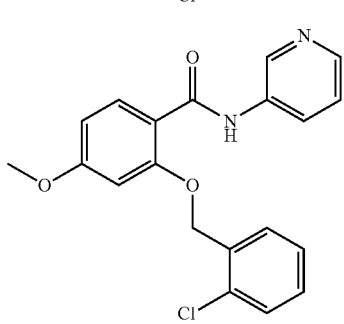

The compounds of the present invention contain alkaline groups which can form salts with acids. Thus salt derivatives can be formed by ordinary means. That includes organic acid salts such as acetate, citrate, fumarate, maleate, oxalate, malate, citrate, succinate, tartrate, lactate, camphor sulfonate, benzene sulfonate, p-toluenesulfonate, methanesulfonate, trifluoroacetate, triflate, and the like; inorganic acid salts such as hydrohalic acids (hydrofluoric acid, hydrochloric acid, hydrobromic acid, hydroiodic acid), sulfate, phosphate, nitrate and the like, or with amino acids, such as glutamic acid and aspartic acid to form glutamate and aspartate. Preferred salts are the hydrochloride and the hydrobromide.

Solvates of 2-alkoxy benzene formyl arylamines compounds are also protected by the present invention. Preferred solvates are water, ethanol, and methanol.

The second aim of the present invention is to show the use of 2-alkoxy benzene formyl arylamines in preparing SMS small-molecule inhibitors. This invention evaluate SMS inhibitory activity of 2-alkoxy benzene formyl arylamines as scheme I through HPLC fluorogenic quantitative detecting method reported (Xiaodong Deng; Hong Sun; et al. *Analytical Letters*, 2012, 45:12, 1581-1589), which can make it possible to calculate the catalytic activity difference of SMS treated with inhibitors or not through content changes of NBD-ceramide and NBD-sphingomyelin.

Activity tests with HPLC fluorogenic quantitative detecting method show that 2-alkoxy benzene formyl arylamines as scheme I has a sub-micromolar sphingomyelin synthase inhibitory activity and are effective constituents which can inhibit SMS. Inhibitory activity data obtained by HPLC fluorogenic quantitative detecting method are listed below:

1) the inhibition rate of 2-(2-fluoro-benzyloxy)-N-(pyridin-3-yl) benzamide (scheme I-1) at 5 μM was 53.8%;
2) the inhibition rate of 2-(3-fluoro-benzyloxy)-N-(pyridin-3-yl) benzamide (scheme I-2) at 5 μM was 69.3%;
3) the inhibition rate of 2-(3-nitro-benzyloxy)-N-(pyridin-3-yl) benzamide (scheme I-3) at 50 μM was 64.6%;
4) the inhibition rate of 2-(3-cyano-benzyloxy)-N-(pyridin-3-yl) benzamide (scheme I-4) at 50 μM was 66.0%;
5) the inhibition rate of 2-((4-methoxy) benzyloxy)-N-(pyridin-3-yl) benzamide (scheme I-5) at 50 μM was 23.0%;
6) the inhibition rate of 2-(2-cyano-benzyloxy)-N-(pyridin-3-yl) benzamide (scheme I-6) at 50 μM was 50.0%;
7) the inhibition rate of 2-(3-chloro-benzyloxy)-N-(pyridin-3-yl) benzamide (scheme I-7) at 5 μM was 70.6%;
8) the inhibition rate of 2-(3-bromo-benzyloxy)-N-(pyridin-3-yl) benzamide (scheme I-8) at 50 μM was 67.1%;
9) the inhibition rate of 2-(4-bromo-benzyloxy)-N-(pyridin-3-yl) benzamide (scheme I-9) at 50 μM was 14.7%;
10) the inhibition rate of 2-((3-methyl) benzyloxy)-N-(pyridin-3-yl) benzamide (scheme I-10) at 50 μM was 69.5%;
11) the inhibition rate of 2-((2-methyl) benzyloxy)-N-(pyridin-3-yl) benzamide (scheme I-11) at 5 μM was 71.3%;
12) the inhibition rate of 2-((2-nitro) benzyloxy)-N-(pyridin-3-yl) benzamide (scheme I-12) at 50 μM was 35.5%;
13) the inhibition rate of 2-((4-nitro) benzyloxy)-N-(pyridin-3-yl) benzamide (scheme I-13) at 50 μM was 11.8%;
14) the inhibition rate of 2-((4-methylphenyl) benzyloxy)-N-(pyridin-3-yl) benzamide (scheme I-14) at 50 μM was 69.0%;
15) the inhibition rate of 2-((4-cyanobenzyl) benzyloxy)-N-(pyridin-3-yl) benzamide (scheme I-15) at 50 μM was 15.0%;
16) the inhibition rate of 2-((2-chloro-5-fluoro) benzyloxy)-N-(pyridin-3-yl) benzamide (scheme I-16) at 5 μM was 75.7%;
17) the inhibition rate of 2-((2,6-dichlorophenyl) benzyloxy)-N-(pyridin-3-yl) benzamide (scheme I-17) at 5 μM was 77.2%;
18) the inhibition rate of 2-((2-fluoro-3-chloro) benzyloxy)-N-(pyridin-3-yl) benzamide (scheme I-18) at 5 μM was 55.2%;
19) the inhibition rate of 4-((2-(pyridin-3-ylcarbamoyl) phenoxy) methyl) benzoate (scheme I-19) at 10 μM was 2.9%;
20) the inhibition rate of 2-((4-trifluoromethyl) benzyloxy)-N-(pyridin-3-yl) benzamide (scheme I-20) at 10 μM was 3.9%;
21) the inhibition rate of 2-((5-fluoro-2-methyl) benzyloxy)-N-(pyridin-3-yl) benzamide (scheme I-21) at 10 μM was 84.7%;

22) the inhibition rate of 2-(3-((2-(pyridin-3-ylcarbamoyl) phenoxy) methyl) phenoxy) acetate (scheme I-22) at 10 μM was 15.3%;

23) the inhibition rate of 2-((3-methoxy) benzyloxy)-N-(pyridin-3-yl) benzamide (scheme I-23) at 10 μM was 59.8%;

24) the inhibition rate of 2-((2-methoxy) benzyloxy)-N-(pyridin-3-yl) benzamide (scheme I-24) at 10 μM was 89.4%;

25) the inhibition rate of 2-((2,5-dimethoxy) benzyloxy)-N-(pyridin-3-yl) benzamide (scheme I-25) at 10 μM was 78.9%;

26) the inhibition rate of 2-((2-benzyloxy) benzyloxy)-N-(pyridin-3-yl) benzamide (scheme I-26) at 10 μM was 76.9%;

27) the inhibition rate of 2-((2-ethyl) benzyloxy)-N-(pyridin-3-yl) benzamide (scheme I-27) at 5 μM was 78.4%;

28) the inhibition rate of 2-((4-ethyl) benzyloxy)-N-(pyridin-3-yl) benzamide (scheme I-28) at 10 μM was 10.1%;

29) the inhibition rate of 2-((2,6-dimethyl) benzyloxy)-N-(pyridin-3-yl) benzamide (scheme I-29) at 10 μM was 88.8%;

30) the inhibition rate of 2-((2-ethoxy) benzyloxy)-N-(pyridin-3-yl) benzamide (scheme I-30) at 10 μM was 86.3%;

31) the inhibition rate of 2-((2-methoxy-5-chloro) benzyloxy)-N-(pyridin-3-yl) benzamide (scheme I-31) at 10 μM was 92.4%;

32) the inhibition rate of 2-((2-chloro-6-fluoro) benzyloxy)-N-(pyridin-3-yl) benzamide (scheme I-32) at 10 μM was 82.3%;

33) the inhibition rate of 2-((2,5-dichloro) benzyloxy)-N-(pyridin-3-yl) benzamide (scheme I-33) at 10 μM was 87.9%;

34) the inhibition rate of 2-(2-(4-chlorobutoxy) benzyloxy)-N-(pyridin-3-yl) benzamide (scheme I-34) at 10 μM was 85.5%;

35) the inhibition rate of 2-(2-(5-chloro-pentoxy) benzyloxy)-N-(pyridin-3-yl) benzamide (scheme I-35) at 10 μM was 91.3%;

36) the inhibition rate of 2-(2-(6-Chloro-hexyloxy) benzyloxy)-N-(pyridin-3-yl) benzamide (scheme I-36) at 10 μM was 91.5%;

37) the inhibition rate of 2-((2-hexyloxy) benzyloxy)-N-(pyridin-3-yl) benzamide (scheme I-37) at 10 μM was 90.2%;

38) the inhibition rate of 2-((2-heptyloxy) benzyloxy)-N-(pyridin-3-yl) benzamide (scheme I-38) at 10 μM was 90.5%;

39) the inhibition rate of 2-((5-chloro-hexyloxy) benzyloxy)-N-(pyridin-3-yl) benzamide (scheme I-39) at 5 μM was 85.5%;

40) the inhibition rate of 2-((5-chloro-2-heptyloxy) benzyloxy)-N-(pyridin-3-yl) benzamide (scheme I-40) at 5 μM was 87.1%;

41) the inhibition rate of 2-((3-trifluoromethyl) benzyloxy)-N-(pyridin-3-yl) benzamide (scheme I-41) at 10 μM was 10.0%;

42) the inhibition rate of 2-((2-trifluoromethyl) benzyloxy)-N-(pyridin-3-yl) benzamide (scheme I-42) at 5 μM was 65.5%;

43) the inhibition rate of 2-((5-chloro-2-methyl) benzyloxy)-N-(pyridin-3-yl) benzamide (scheme I-43) at 5 μM was 74.8%;

44) the inhibition rate of 2-((3-chloro-2-methyl) benzyloxy)-N-(pyridin-3-yl) benzamide (scheme I-44) at 5 μM was 47.0%;

45) the inhibition rate of 2-((naphthalen-1-yl) methoxy)-N-(pyridin-3-yl) benzamide (scheme I-45) at 10 μM was 78.0%;

46) the inhibition rate of 4-((2-(pyridin-3-ylcarbamoyl) phenoxy) methyl) benzoic acid (scheme I-46) at 10 μM was 2.6%;

47) the inhibition rate of 2-(2-((2-(pyridin-3-ylcarbamoyl) phenoxy) methyl) phenoxy) acetic acid (scheme I-47) at 10 μM was 7.4%;

48) the inhibition rate of 2-(3-((2-(pyridin-3-ylcarbamoyl) phenoxy) methyl) phenoxy) acetic acid (scheme I-48) at 10 μM was 3.0%;

49) the inhibition rate of 2-((5-chloro-2-(3-methoxy-propoxy)) benzyloxy)-N-(pyridin-3-yl) benzamide (scheme I-49) at 10 μM was 75.3%;

50) the inhibition rate of 2-((5-chloro-2-(2-methoxy-ethoxy)) benzyloxy)-N-(pyridin-3-yl) benzamide (scheme I-50) at 10 μM was 54.2%;

51) the inhibition rate of 2-((5-chloro-2-(2-morpholino-ethoxy)) benzyloxy)-N-(pyridin-3-yl) benzamide (scheme I-51) at 10 μM was 24.9%;

52) the inhibition rate of 2-benzyloxy-N-(pyridin-2-yl) benzamide (scheme I-52) at 100 μM was 60.1%;

53) the inhibition rate of 2-benzyloxy-N-(pyrimidin-5-yl) benzamide (scheme I-53) at 10 μM was 38.4%;

54) the inhibition rate of 5-chloro-2-((2,6-dichlorophenyl) benzyloxy)-N-(pyridin-3-yl) benzamide (scheme I-54) at 10 μM was 42.3%;

55) the inhibition rate of 5-chloro-2-((2-chloro-5-fluoro) benzyloxy)-N-(pyridin-3-yl) benzamide (scheme I-55) at 10 μM was 31.7%;

56) the inhibition rate of 4-Chloro-2-(2-chloro-benzyloxy)-N-(pyridin-3-yl) benzamide (scheme I-56) at 10 μM was 20.0%;

57) the inhibition rate of 2-(2-chloro-benzyloxy)-5-nitro-N-(pyridin-3-yl) benzamide (scheme I-57) at 10 μM was 1.7%;

58) the inhibition rate of 4-bromo-2-(2-chloro-benzyloxy)-N-(pyridin-3-yl) benzamide (scheme I-58) at 10 μM was 19.4%;

59) the inhibition rate of 2-(2-chloro-benzyloxy)-5-methoxy-N-(pyridin-3-yl) benzamide (scheme I-59) at 10 μM was 7.2%;

60) the inhibition rate of 2-(2-chloro-benzyloxy)-4-methoxy-N-(pyridin-3-yl) benzamide (scheme I-60) at 10 μM was 13.3%.

The further aim of this invention is to provide the use of 2-alkoxy benzene formyl arylamines as scheme I and their salts or solvate in preventing and treating atherosclerosis, fatty liver, obesity, type II diabetes and other diseases caused by SM abnormal increase.

The present invention experimentally confirmed that compared to existing SMS small-molecular inhibitors D609 and D2, the compounds disclosed in the invention are better in both inhibitory activity and physicochemical properties such as solvability and stability; furthermore, there is nopotential toxic group in these compounds, which suggests few potential reverse effects, thus can be used to prevent and treat atherosclerosis, fatty liver, obesity, type II diabetes and other diseases caused by SM abnormal increase.

The drugs mentioned above may also contain one or more pharmaceutically acceptable carriers, that is, conventional diluents, excipients, fillers, binders, humectants, disintegrants, absorption enhancers, surfactants, adsorption carrier, lubricants and the like, and flavoring agents, sweetening and the like if necessary.

The beneficial effect of the present invention is that the 2-alkoxy-benzoyl aromatic amine compounds are novel-structured SMS inhibitors which have sub-micromolar sphingomyelin synthase inhibitory activities and have a real potentiality and prospects to be developed into drugs to cure atherosclerosis, fatty liver, obesity, and type II diabetes.

DETAILED DESCRIPTION

Application Case 1: Preparation of 2-((2,6-dichloro-phenyl) benzyloxy)-N-(pyridin-3-yl) Benzamide (Scheme I-17)

1. Synthesis of 2-benzyloxy-benzoic Acid Methyl Ester (Compound 3a)

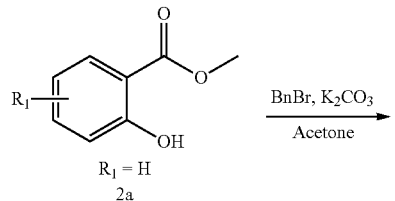

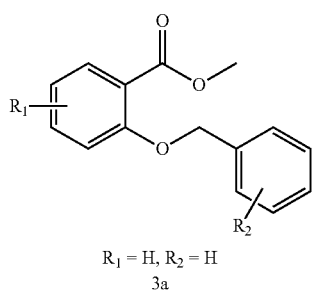

11.4 g (75 mmol, 1.0 eq) methyl salicylate was dissolved in 200 ml acetone at room temperature; the mixture was stirred uniformly before 15.52 g (112.5 mmol, 1.5 eq) potassium carbonate was added in and then slowly add 13.5 g (78.75 mmol, 1.05 eq) benzyl bromide dropwise. After the addition was complete, the reaction was heated to reflux for 3 hours. The reaction was monitored by TLC. Stop heating when the starting materials disappeared and let the mixture cool to room temperature. Remove the solid by vacuum filtration, wash the filter cake twice with acetone. The combined filtrate was concentrated to give a colorless transparent oil 18.06 g, yield 99.4%. The crude product was used without purification in the next step directly. MS(ESI) (m/z): 243.1 (M+H)$^+$.

2. Synthesis of 2-benzyloxy-benzoic Acid (Compound 4a)

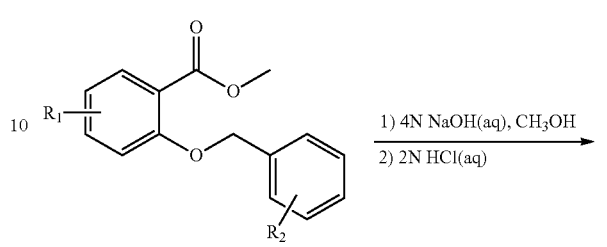

18.17 g (75 mmol, 1.0 eq) 2-benzyloxy-benzoic acid methyl ester (compound 3a) was dissolved in 75 ml methanol and stirred uniformly. Then 75 ml sodium hydroxide aqueous solution (4 mol/L) was dropwise added at room temperature to the mixture. After 4.5 hours' reaction when the reaction system turn to the clear and transparent solution; TLC showed no starting material. Remove the methanol by vacuum distillation, add to the system 2M hydrochloric acid solution to regulate the pH value to 5~6 for solid to separate out. Then the solid was filtered and dried under vacuum to give 15.0 g of white solid, yield 87.6%. The crude product was used without purification in the next step directly. MS(ESI) (m/z): 227.1 (M−H)$^-$.

3. Synthesis of 2-benzyloxy-N-(pyridin-3-yl) Benzamide (Compound 6a)

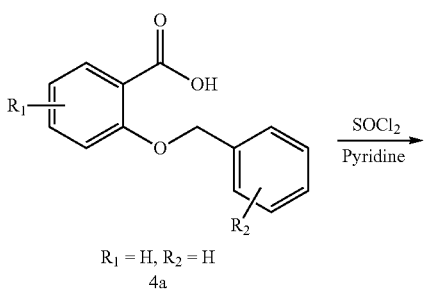

4. Synthesis of 2-hydroxy-N-(pyridin-3-yl) Benzamide (Compound 7)

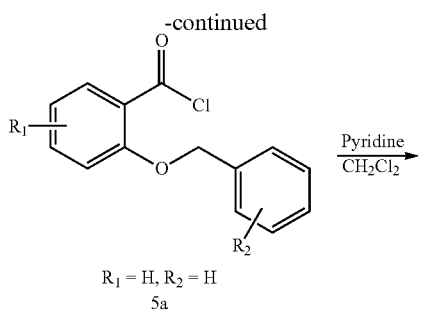

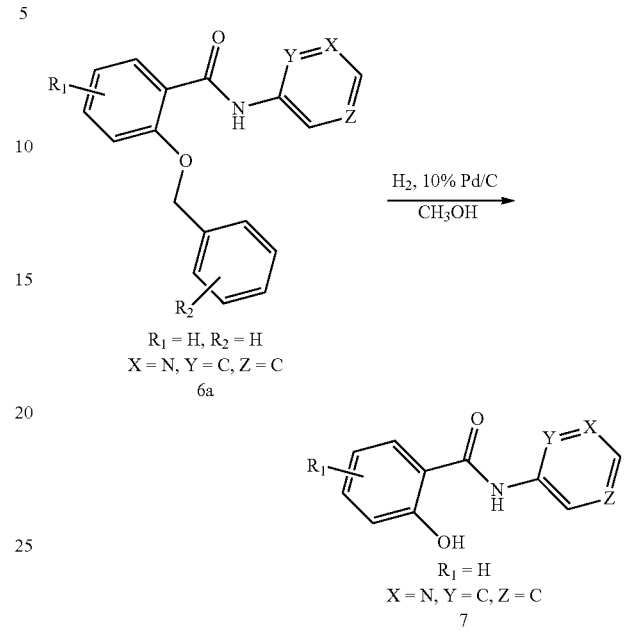

Add 0.55 g (2.4 mmol, 1.2 eq) 2-benzyloxy-benzoic acid (compound 4a) and 7.25 ml disulfur dichloride to a dry one-necked flask. After stirring about 5 minutes, add two drops of pyridine. The reaction system was then heated to reflux for 2.5 hours; TLC showed no starting material existed. Then disulfur dichloride was removed by vacuum distillation to obtain a pale yellow wax-like solid (compound 5a). The crude product was used without purification in the next step directly.

Dissolve 0.19 g (2 mmol, 1.0 eq) 3-aminopyridine into 10 ml dry dichloromethane, then add 0.32 ml (4 mmol, 2.0 eq) pyridine and stir well. Add dichloromethane containing compound 5a dropwise to the mixture under the condition of ice water bath. After reacting of 2 hours in room temperature, the reaction mixture was washed with water twice followed by saturated sodium chloride solution twice, then dried with anhydrous sodium sulfate and desolventizing to gain 0.53 g light yellow solid. The crude product was purified by recrystallization with a mixed solvent of PE:EA=2:1 to give 0.28 g of white powder-like solid (compound 6a), yield 46.7%.

The structure is confirmed correct and data are as follow: m.p 107.6-108.9° C. MS(ESI)(m/z): 305.2 (M+H)$^+$. $^1$H NMR (400 MHz, DMSO-d$_6$) δ ppm 10.36 (s, 1H), 8.68 (d, J=2.3 Hz, 1H), 8.27 (dd, J=4.7, 1.3 Hz, 1H), 8.10 (d, J=8.3 Hz, 1H), 7.69 (dd, J=7.6, 1.6 Hz, 1H), 7.57-7.50 (m, 3H), 7.40-7.32 (m, 4H), 7.30 (d, J=8.3 Hz, 1H), 7.11 (t, J=7.4 Hz, 1H), 5.25 (s, 2H).

5.01 g (16.46 mmol, 1.0 eq) 2-benzyloxy-N-(pyridin-3-yl) benzamide (Compound 6a) was dissolved in 85 ml methanol, then 10% Pd/C was added. The mixture was stirred 2 hours under three atmospheres of hydrogen pressure. After the Pd/C had been removed by suction filtration, methanol was removed by vacuum distillation to obtain 3.47 g white powder-like solid (compound 7), yield 98.6%.

The structure is confirmed correct and data are as follow: MS(ESI) (m/z): 215.1 (M+H)$^+$. $^1$H NMR (400 MHz, DMSO-d$_6$) δ ppm 11.65 (s, 1H), 10.53 (s, 1H), 8.88 (d, J=2.4 Hz, 1H), 8.35 (dd, J=4.7, 1.4 Hz, 1H), 8.17 (ddd, J=8.3, 2.4, 1.5 Hz, 1H), 7.95 (dd, J=7.9, 1.6 Hz, 1H), 7.49-7.39 (m, 2H), 7.04-6.95 (m, 2H).

5. Synthesis of 2-((2,6-dichlorophenyl) benzyloxy)-N-(pyridin-3-yl) Benzamide (Scheme I-17)

0.21 g (1.0 mmol, 1.0 eq) 2-hydroxy-N-(pyridin-3-yl) benzamide (Compound 7) was dissolved in 6 ml acetone, in the mixture were added 0.28 g (2.0 mmol, 2.0 eq) potassium carbonate and 0.24 g (1.0 mmol, 1.0 eq) 2,6-dichloro benzyl bromide (compound 8-1q). After reacting for an hour, remove acetone by vacuum distillation. Add water and EA to extract and wash the organic phase twice with saturated sodium chloride solution, then dry with anhydrous sodium sulfate and desolventizing to gain 0.34 g brown oily material. The crude product was then purified by column chromatography purification using mobile phase of PE:EA=2:1 to gain 0.24 g light yellow powder-like solid (Scheme I-17), yield 64.9%.

The structure is confirmed correct and data are as follow: m.p 115.0-116.4° C. MS(ESI) (m/z): 373.0 (M+H)$^+$. $^1$H NMR (400 MHz, DMSO-d$_6$) δ ppm 10.16 (s, 1H), 8.51 (d, J=2.4 Hz, 1H), 8.25 (dd, J=4.7, 1.4 Hz, 1H), 8.05-7.98 (m, 1H), 7.71 (dd, J=7.6, 1.6 Hz, 1H), 7.63-7.53 (m, 3H), 7.47 (dd, J=9.0, 7.0 Hz, 2H), 7.33 (dd, J=8.3, 4.7 Hz, 1H), 7.18 (t, J=7.3 Hz, 1H), 5.43 (s, 2H).

Application Case 2: Synthesis of Scheme I-1, I-2, I-3, I-4, I-5, I-6, I-7, I-8, I-9, I-10, I-11, I-12, I-13, I-14, I-15, I-16, I-18, I-19, I-20

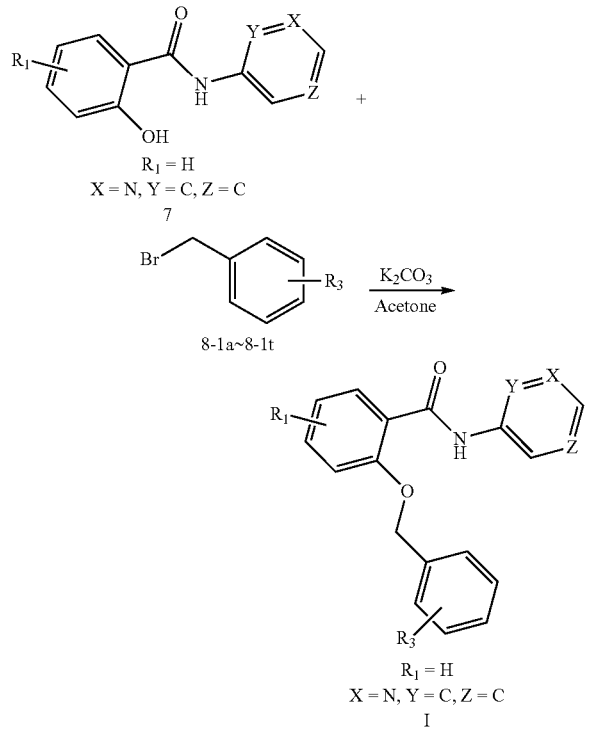

| Scheme I | R$_3$ | Yield (%) |
| --- | --- | --- |
| I-1 | 2-F | 71.9 |
| I-2 | 3-F | 56.3 |
| I-3 | 3-NO$_2$ | 71.4 |
| I-4 | 3-CN | 81.0 |
| I-5 | 4-OMe | 44.9 |
| I-6 | 2-CN | 30.4 |
| I-7 | 3-Cl | 64.9 |
| I-8 | 3-Br | 78.9 |
| I-9 | 4-Br | 78.9 |
| I-10 | 3-Me | 81.3 |
| I-11 | 2-Me | 46.9 |
| I-12 | 2-NO$_2$ | 80.0 |
| I-13 | 4-NO$_2$ | 91.4 |
| I-14 | 4-Me | 87.5 |
| I-15 | 4-CN | 97.0 |
| I-16 | 2-Cl,5-F | 72.2 |
| I-18 | 2-F,3-Cl | 75.0 |
| I-19 | 4-COOEt | 31.6 |
| I-20 | 4-CF$_3$ | 84.2 |

Referring to reaction conditions of the fifth step of synthesizing scheme I-17 in Application case 1, starting from 2-hydroxy-N-(pyridin-3-yl) benzamide (Compound 7) and commercially available corresponding substituted benzyl bromides (compound 8-1a~8-1t) to obtain scheme I-1 to I-16 and scheme I-18 to I-20, that is:

2-(2-fluoro-benzyloxy)-N-(pyridin-3-yl) benzene carboxamide (Scheme I-1);

2-(3-fluoro-benzyloxy)-N-(pyridin-3-yl) benzamide (Scheme I-2);

2-(3-nitro-benzyloxy)-N-(pyridin-3-yl) benzamide (Scheme I-3);

2-(3-cyano-benzyloxy)-N-(pyridin-3-yl) benzamide (Scheme I-4);

2-((4-methoxy) benzyloxy)-N-(pyridin-3-yl) benzamide (Scheme I-5);

2-(2-cyanobenzyloxy)-N-(pyridin-3-yl) benzamide (Scheme I-6);

2-(3-chloro-benzyloxy)-N-(pyridin-3-yl) benzamide (Scheme I-7);

2-(3-bromo-benzyloxy)-N-(pyridin-3-yl) benzamide (Scheme I-8);

2-(4-bromo-benzyloxy)-N-(pyridin-3-yl) benzamide (scheme I-9);

2-((3-methyl) benzyloxy)-N-(pyridin-3-yl) benzamide (scheme I-10);

2-((2-methyl) benzyloxy yl)-N-(pyridin-3-yl) benzamide (Scheme I-11);

2-((2-nitro) benzyloxy)-N-(pyridin-3-yl) benzamide (Scheme I-12);

2-((4-nitro) benzyloxy)-N-(pyridin-3-yl) benzamide (Scheme I-13);

2-((4-methyl) benzyloxy)-N-(pyridin-3-yl) benzamide (Scheme I-14);

2-((4-cyano) benzyloxy)-N-(pyridin-3-yl) benzamide (Scheme I-15);

2-((2-chloro-5-fluoro) benzyloxy)-N-(pyridin-3-yl) benzamide (Scheme I-16);

2-((2-fluoro-3-chloro) benzyloxy)-N-(pyridin-3-yl) benzamide (Scheme I-18);

4-((2-(pyridin-3-ylcarbamoyl) phenoxy) methyl) benzene carboxylic acid ethyl ester (Scheme I-19);

2-((4-trifluoromethyl) benzyloxy)-N-(pyridin-3-yl) benzamide (Scheme I-20).

The structures were confirmed correct and data are as follow:

Scheme I-1 m.p 101.6-102.5° C. MS(ESI) (m/z): 323.2 (M+H)$^+$. $^1$H NMR (400 MHz, DMSO-d$_6$) δ ppm 10.56 (s, 1H), 8.86 (d, J=1.8 Hz, 1H), 8.39 (dd, J=4.9, 1.1 Hz, 1H), 8.22 (d, J=8.4 Hz, 1H), 7.68 (dd, J=7.6, 1.7 Hz, 1H), 7.66-7.61 (m, 1H), 7.60-7.53 (m, 2H), 7.44-7.34 (m, 2H), 7.25 (dd, J=9.8, 8.9 Hz, 1H), 7.19 (td, J=7.5, 0.8 Hz, 1H), 7.14 (t, J=7.5 Hz, 1H), 5.33 (s, 2H).

Scheme I-2 m.p 102.8-104.2° C. MS(ESI) (m/z): 323.0 (M+H)$^+$. $^1$H NMR (400 MHz, DMSO-d$_6$) δ ppm 10.40 (s, 1H), 8.76 (d, J=2.4 Hz, 1H), 8.29 (dd, J=4.7, 1.4 Hz, 1H), 8.18-8.10 (m, 1H), 7.67 (dd, J=7.6, 1.6 Hz, 1H), 7.57-7.50 (m, 1H), 7.45-7.34 (m, 4H), 7.27 (d, J=8.3 Hz, 1H), 7.19-7.09 (m, 2H), 5.27 (s, 2H).

Scheme I-3 m.p 138.2-141.1° C. MS(ESI) (m/z): 350.0 (M+H)$^+$. $^1$H NMR (400 MHz, DMSO-d$_6$) δ ppm 10.43 (s, 1H), 8.79 (s, 1H), 8.27 (d, J=4.6 Hz, 1H), 8.19 (d, J=7.3 Hz, 2H), 8.14 (d, J=7.2 Hz, 1H), 7.75 (d, J=7.8 Hz, 2H), 7.62 (d, J=7.5 Hz, 1H), 7.50 (t, J=7.9 Hz, 1H), 7.36 (dd, J=7.7, 4.8 Hz, 1H), 7.23 (d, J=8.3 Hz, 1H), 7.10 (t, J=7.4 Hz, 1H), 5.39 (s, 2H).

Scheme I-4 m.p 150.2-152.6° C. MS(ESI) (m/z): 330.1 (M+H)$^+$. $^1$H NMR (400 MHz, DMSO-d$_6$) δ ppm 10.41 (s, 1H), 8.80 (s, 1H), 8.27 (d, J=4.1 Hz, 1H), 8.11 (d, J=8.2 Hz, 1H), 7.97 (s, 1H), 7.84 (d, J=7.8 Hz, 1H), 7.77 (d, J=7.7 Hz, 1H), 7.62 (d, J=7.4 Hz, 1H), 7.59-7.47 (m, 2H), 7.36 (dd, J=8.1, 4.7 Hz, 1H), 7.24 (d, J=8.3 Hz, 1H), 7.10 (t, J=7.4 Hz, 1H), 5.27 (s, 2H).

Scheme I-5 m.p 114.9-118.4° C. MS(ESI) (m/z): 335.0 (M+H)$^+$. $^1$H NMR (400 MHz, DMSO-d$_6$) δ ppm 10.34 (s, 1H), 8.63 (s, 1H), 8.25 (d, J=4.6 Hz, 1H), 8.07 (d, J=8.4 Hz, 1H), 7.68 (d, J=7.6 Hz, 1H), 7.52 (t, J=7.9 Hz, 1H), 7.47 (d, J=8.5 Hz, 2H), 7.34 (dd, J=8.3, 4.7 Hz, 1H), 7.29 (d, J=8.3 Hz, 1H), 7.08 (t, J=7.5 Hz, 1H), 6.91 (d, J=8.5 Hz, 2H), 5.15 (s, 2H), 3.72 (s, 3H).

Scheme I-6 m.p 122.8-125.2° C. MS(ESI) (m/z): 330.1 (M+H)$^+$. $^1$H NMR (400 MHz, DMSO-d$_6$) δ ppm 10.32 (s, 1H), 8.67 (s, 1H), 8.25 (d, J=4.2 Hz, 1H), 8.08 (d, J=8.3 Hz, 1H), 7.88 (d, J=7.6 Hz, 1H), 7.78 (t, J=10.8 Hz, 1H), 7.67 (dd, J=12.1, 7.0 Hz, 2H), 7.53 (dd, J=9.0, 4.4 Hz, 2H), 7.33 (dd, J=12.6, 6.5 Hz, 2H), 7.13 (t, J=7.4 Hz, 1H), 5.41 (s, 2H).

Scheme I-7 m.p 125.1-125.6° C. MS(ESI) (m/z): 339.2 (M+H)$^+$. $^1$H NMR (400 MHz, DMSO-d$_6$) δ ppm 10.40 (s, 1H), 8.79 (d, J=2.4 Hz, 1H), 8.29 (dd, J=4.7, 1.4 Hz, 1H), 8.20-8.07 (m, 1H), 7.66 (dd, J=7.7, 1.6 Hz, 2H), 7.58-7.50 (m, 1H), 7.50-7.44 (m, 1H), 7.43-7.33 (m, 3H), 7.28 (d, J=8.3 Hz, 1H), 7.12 (t, J=7.4 Hz, 1H), 5.25 (s, 2H).

Scheme I-8 m.p 151.4-152.4° C. MS(ESI) (m/z): 384.0 (M+H)$^+$. $^1$H NMR (400 MHz, DMSO-d$_6$) δ ppm 10.39 (s, 1H), 8.78 (s, 1H), 8.26 (d, J=4.6 Hz, 1H), 8.11 (d, J=8.2 Hz, 1H), 7.77 (s, 1H), 7.63 (d, J=7.5 Hz, 1H), 7.51 (dd, J=14.6, 7.6 Hz, 3H), 7.35 (dd, J=8.2, 4.8 Hz, 1H), 7.30 (t, J=7.8 Hz, 1H), 7.25 (d, J=8.4 Hz, 1H), 7.10 (t, J=7.4 Hz, 1H), 5.22 (s, 2H).

Scheme I-9 m.p 147.2-148.7° C. MS(ESI) (m/z): 384.0 (M+H)$^+$. $^1$H NMR (400 MHz, DMSO-d$_6$) δ ppm 10.36 (s, 1H), 8.72 (d, J=2.3 Hz, 1H), 8.26 (d, J=4.6 Hz, 1H), 8.10 (d, J=8.3 Hz, 1H), 7.63 (d, J=7.5 Hz, 1H), 7.54 (d, J=8.3 Hz, 2H), 7.48 (t, J=8.9 Hz, 3H), 7.35 (dd, J=8.3, 4.7 Hz, 1H), 7.24 (d, J=8.4 Hz, 1H), 7.08 (t, J=7.5 Hz, 1H), 5.21 (s, 2H).

Scheme I-10 m.p 151.9-153.6° C. MS(ESI) (m/z): 319.0 (M+H)$^+$. $^1$H NMR (400 MHz, DMSO-d$_6$) δ ppm 10.37 (s, 1H), 8.68 (s, 1H), 8.26 (d, J=4.7 Hz, 1H), 8.11 (d, J=8.3 Hz, 1H), 7.67 (d, J=7.6 Hz, 1H), 7.52 (t, J=7.8 Hz, 1H), 7.34 (t, J=6.4 Hz, 2H), 7.28 (d, J=8.1 Hz, 2H), 7.22 (t, J=7.5 Hz, 1H), 7.10 (dd, J=12.8, 6.3 Hz, 2H), 5.18 (s, 2H), 2.20 (s, 3H).

Scheme I-11 m.p 95.9-98.0° C. MS(ESI) (m/z): 319.2 (M+H)$^+$. $^1$H NMR (400 MHz, DMSO-d$_6$) δ ppm 10.37 (s, 1H), 8.61 (d, J=2.4 Hz, 1H), 8.27 (dd, J=4.7, 1.4 Hz, 1H), 8.09-8.02 (m, 1H), 7.69 (dd, J=7.6, 1.7 Hz, 1H), 7.58-7.52 (m, 1H), 7.50 (d, J=7.5 Hz, 1H), 7.39-7.32 (m, 2H), 7.28-7.21 (m, 2H), 7.15 (ddd, J=17.3, 11.2, 4.7 Hz, 2H), 5.26 (s, 2H), 2.34 (s, 3H).

Scheme I-12 m.p 110.7-112.9° C. MS(ESI) (m/z): 350.0 (M+H)$^+$. $^1$H NMR (400 MHz, DMSO-d$_6$) δ ppm 10.42 (s, 1H), 8.76 (d, J=2.3 Hz, 1H), 8.28 (dd, J=4.7, 1.4 Hz, 1H), 8.13 (dt, J=8.2, 2.0 Hz, 2H), 7.84 (d, J=7.5 Hz, 1H), 7.69-7.54 (m, 3H), 7.52-7.45 (m, 1H), 7.36 (dd, J=8.3, 4.7 Hz, 1H), 7.24 (d, J=8.3 Hz, 1H), 7.11 (td, J=7.5, 0.7 Hz, 1H), 5.60 (s, 2H).

Scheme I-13 m.p 142.4-144.6° C. MS(ESI) (m/z): 350.0 (M+H)$^+$. $^1$H NMR (400 MHz, DMSO-d$_6$) δ ppm 10.43 (s, 1H), 8.79 (s, 1H), 8.27 (d, J=4.6 Hz, 1H), 8.19 (d, J=7.3 Hz, 2H), 8.14 (d, J=7.2 Hz, 2H), 7.75 (d, J=7.8 Hz, 2H), 7.62 (d, J=7.5 Hz, 1H), 7.50 (t, J=7.9 Hz, 1H), 7.36 (dd, J=7.7, 4.8 Hz, 1H), 7.23 (d, J=8.3 Hz, 1H), 7.10 (t, J=7.4 Hz, 1H), 5.39 (s, 2H).

Scheme I-14 m.p 133.3-137.6° C. MS(ESI) (m/z): 319.0 (M+H)$^+$. $^1$H NMR (400 MHz, DMSO-d$_6$) δ ppm 10.35 (s, 1H), 8.66 (s, 1H), 8.26 (d, J=4.6 Hz, 1H), 8.08 (d, J=8.3 Hz, 1H), 7.68 (d, J=7.5 Hz, 1H), 7.51 (t, J=7.8 Hz, 1H), 7.41 (d, J=7.2 Hz, 2H), 7.34 (dd, J=7.9, 4.6 Hz, 1H), 7.28 (d, J=8.3 Hz, 1H), 7.15 (d, J=7.2 Hz, 2H), 7.08 (t, J=7.4 Hz, 1H), 5.18 (s, 2H), 2.27 (s, 3H).

Scheme I-15 m.p 139.1-140.5° C. MS(ESI) (m/z): 330.0 (M+H)$^+$. $^1$H NMR (400 MHz, DMSO-d$_6$) δ ppm 10.40 (s, 1H), 8.76 (s, 1H), 8.27 (d, J=4.7 Hz, 1H), 8.12 (d, J=8.3 Hz, 1H), 7.85-7.78 (m, 2H), 7.68 (d, J=7.8 Hz, 2H), 7.62 (d, J=7.5 Hz, 1H), 7.50 (t, J=7.8 Hz, 1H), 7.36 (dd, J=8.2, 4.6 Hz, 1H), 7.22 (d, J=8.3 Hz, 1H), 7.09 (t, J=7.4 Hz, 1H), 5.33 (s, 2H).

Scheme I-16 m.p 118.0-119.2° C. MS(ESI) (m/z): 357.0 (M+H)$^+$. $^1$H NMR (400 MHz, DMSO-d$_6$) δ ppm 10.41 (s, 1H), 8.76 (d, J=2.4 Hz, 1H), 8.29 (dd, J=4.7, 1.4 Hz, 1H), 8.17-8.11 (m, 1H), 7.66 (dd, J=7.5, 1.6 Hz, 1H), 7.59-7.48 (m, 3H), 7.38 (dd, J=8.3, 4.7 Hz, 1H), 7.31 (d, J=8.3 Hz, 1H), 7.25 (td, J=8.5, 3.1 Hz, 1H), 7.15 (t, J=7.4 Hz, 1H), 5.30 (s, 2H). Scheme I-16 hydrochloride m.p 167.3-169.0° C.

Scheme I-18 m.p 149.8-150.6° C. MS(ESI) (m/z): 357.0 (M+H)$^+$. $^1$H NMR (400 MHz, DMSO-d$_6$) δ ppm 10.33 (s, 1H), 8.72 (d, J=2.4 Hz, 1H), 8.28 (dd, J=4.7, 1.4 Hz, 1H), 8.14-8.08 (m, 1H), 7.66 (dd, J=7.6, 1.7 Hz, 1H), 7.63-7.51 (m, 3H), 7.39-7.32 (m, 2H), 7.21 (t, J=7.9 Hz, 1H), 7.14 (t, J=7.5 Hz, 1H), 5.36 (s, 2H).

Scheme I-19 m.p 93.7-97.0° C. MS(ESI) (m/z): 377.0 (M+H)$^+$. $^1$H NMR (400 MHz, DMSO-d$_6$) δ ppm 10.42 (s, 1H), 8.76 (d, J=1.8 Hz, 1H), 8.27 (d, J=4.2 Hz, 1H), 8.18-8.12 (m, 1H), 7.91 (d, J=8.2 Hz, 2H), 7.67-7.60 (m, 3H), 7.54-7.47 (m, 1H), 7.35 (dd, J=8.3, 4.7 Hz, 1H), 7.24 (d, J=8.4 Hz, 1H), 7.09 (t, J=7.5 Hz, 1H), 5.31 (s, 2H), 4.28 (q, J=7.1 Hz, 2H), 1.28 (t, J=7.1 Hz, 3H).

Scheme I-20 m.p 144.6-147.8° C. MS(ESI) (m/z): 373.0 (M+H)$^+$. $^1$H NMR (400 MHz, DMSO-d$_6$) δ ppm 10.41 (s, 1H), 8.77 (d, J=2.1 Hz, 1H), 8.27 (d, J=4.6 Hz, 1H), 8.11 (d, J=8.3 Hz, 1H), 7.76-7.67 (m, 4H), 7.67-7.61 (m, 1H), 7.50 (t, J=7.9 Hz, 1H), 7.35 (dd, J=8.3, 4.7 Hz, 1H), 7.24 (d, J=8.4 Hz, 1H), 7.09 (t, J=7.5 Hz, 1H), 5.34 (s, 2H).

Application Case 3: Synthesis of Scheme I-21, I-22, I-23, I-24, I-25, I-26

1. Synthesis of Compound 8-2a~8-2d

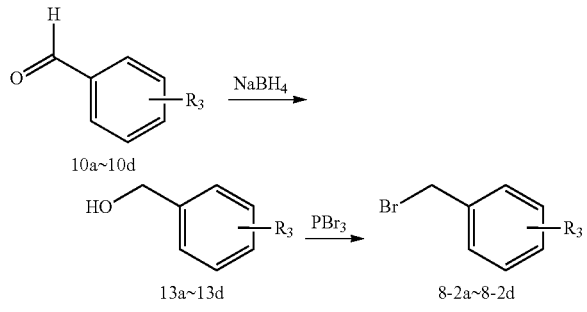

| Compound | R$_3$ |
| --- | --- |
| 8-2a | 2-CH$_3$, 5-F |
| 8-2b | 3-OCH$_3$ |
| 8-2c | 2-OCH$_3$ |
| 8-2d | 2,5-di-OCH$_3$ |

1.10 g (8 mmol, 1.0 eq) 2-methoxy benzaldehyde (Compound 10c) was dissolved in 12 ml anhydrous ethanol, then 0.32 g (8 mmol, 1.0 eq) 96% NaBH$_4$ was added in the mixture. After reacting 3 hours at room temperature, the reaction was quenched with water. Ethanol was removed by vacuum distillation. Then 10 ml water and 20 ml*2 EA were added for extract. The organic phase was washed twice with saturated sodium chloride solution, then dried over anhydrous sodium sulfate and desolventizing to gain 1.02 g colorless transparent oily material (Compound 13c), yield 92.3%. Compound 13a, 13b, and 13d can be obtained in the same way from compound 10a, 10b, and 10d.

1.02 g (7.38 mmol, 1.0 eq) compound 13c was dissolved in 40 ml CH$_2$Cl$_2$, then 0.84 ml (8.90 mmol, 1.2 eq) PBr$_3$ was added under the condition of ice water bath. After reacting for an hour, a little saturated sodium bicarbonate solution was added to wash the organic phase followed by twice wash with saturated sodium chloride solution, then dried over anhydrous sodium sulfate and desolventizing to gain 1.15 g reddish colored oily material (Compound 8-2c), yield 77.5%. The crude product was used without purification in the next step directly. Compound 8-2a, 8-2b, and 8-2d can be obtained in the same way from compound 13a, 13b, and 13d.

Synthesis of Scheme I-21, I-23, I-24 and I-25

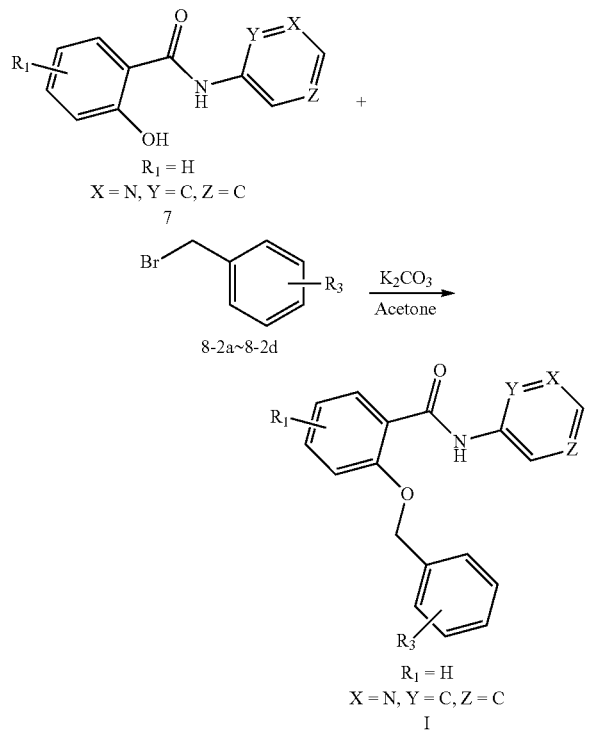

| SchemeI | R$_3$ | Yield (%) |
|---|---|---|
| I-21 | 2-CH$_3$, 5-F | 70.0 |
| I-23 | 3-OCH$_3$ | 76.9 |
| I-24 | 2-OCH$_3$ | 76.2 |
| I-25 | 2,5-di-OCH$_3$ | 27.3 |

0.32 g (1.5 mmol, 1.0 eq) 2-hydroxy-N-(pyridin-3-yl) benzamide (Compound 7) was dissolved in 9 ml acetone, in the mixture was added 0.42 g (3.0 mmol, 2.0 eq) potassium carbonate and 0.30 g (1.5 mmol, 1.0 eq) 2-methoxy-benzyl bromide (Compound 8-2c). After reacting for 1.0 hour, remove acetone by vacuum distillation. Add water and EA to extract and wash the organic phase twice with saturated sodium chloride solution, then dry with anhydrous sodium sulfate and desolventizing to gain brown oily material. The crude product was then purified by column chromatography purification using mobile phase of PE:EA=2:1 to gain 0.27 g white powder-like solid (Scheme I-24), yield 76.2%.

Referring to reaction conditions above, starting from 2-hydroxy-N-(pyridin-3-yl) benzamide (Compound 7) and commercially available corresponding substituted benzyl bromides (compound 8-2a, 8-2a and 8-2t) to obtain scheme I-21, I-23 and scheme I-25, that is: 2-((5-fluoro-2-methyl) benzyloxy)-N-(pyridin-3-yl) benzamide (Scheme I-21); 2-((3-methoxy) benzyloxy)-N-(pyridin-3-yl) benzamide (Scheme I-23); 2-((2,5-dimethoxyphenyl) benzyloxy)-N-(pyridin-3-yl) benzoate amide (Scheme I-25).

The structures were confirmed correct and data are as follow:

Scheme I-21 m.p 156.2-157.7° C. MS(ESI) (m/z): 337.0 (M+H)$^+$. $^1$H NMR (600 MHz, DMSO-d$_6$) δ ppm 11.05 (d, J=6.3 Hz, 1H), 9.21 (s, 1H), 8.59 (d, J=5.3 Hz, 1H), 8.47 (d, J=7.7 Hz, 1H), 7.90 (dt, J=9.1, 4.7 Hz, 1H), 7.63 (dd, J=7.5, 1.7 Hz, 1H), 7.60-7.55 (m, 1H), 7.36 (d, J=8.4 Hz, 1H), 7.28 (dd, J=10.0, 2.7 Hz, 1H), 7.23 (dd, J=8.2, 6.0 Hz, 1H), 7.14 (t, J=7.4 Hz, 1H), 7.02 (td, J=8.5, 2.8 Hz, 1H), 5.24 (s, 2H), 2.28 (s, 3H). Scheme I-21 hydrochloride m.p 156.2-157.7° C.

Scheme I-23 m.p 168.6-171.0° C. MS(ESI) (m/z): 335.0 (M+H)$^+$. $^1$H NMR (400 MHz, DMSO-d$_6$) δ ppm 10.37 (s, 1H), 8.72 (d, J=2.3 Hz, 1H), 8.28 (dd, J=4.7, 1.3 Hz, 1H), 8.11 (d, J=8.4 Hz, 1H), 7.69 (dd, J=7.6, 1.6 Hz, 1H), 7.59-7.48 (m, 1H), 7.36 (dd, J=8.3, 4.7 Hz, 1H), 7.29 (dd, J=12.8, 5.0 Hz, 2H), 7.18-7.03 (m, 3H), 6.89 (dd, J=8.1, 2.2 Hz, 1H), 5.23 (s, 2H), 3.67 (s, 3H).

Scheme I-24 m.p 136.4-137.6° C. MS(ESI) (m/z): 335.0 (M+H)$^+$. $^1$H NMR (600 MHz, DMSO-d$_6$) δ ppm 10.34 (s, 1H), 8.59 (d, J=2.4 Hz, 1H), 8.28 (dd, J=4.7, 1.4 Hz, 1H), 8.09-8.01 (m, 1H), 7.76 (dd, J=7.6, 1.7 Hz, 1H), 7.56-7.50 (m, 2H), 7.38-7.31 (m, 3H), 7.14-7.06 (m, 2H), 6.93 (td, J=7.4, 0.7 Hz, 1H), 5.26 (s, 2H), 3.78 (s, 3H).

Scheme I-25 MS(ESI) (m/z): 365.1 (M+H)$^+$. $^1$H NMR (400 MHz, DMSO-d$_6$) δ ppm 10.38 (s, 1H), 8.65 (s, 1H), 8.26 (d, J=4.1 Hz, 1H), 8.08 (d, J=8.2 Hz, 1H), 7.72 (d, J=7.4 Hz, 1H), 7.52 (t, J=7.7 Hz, 1H), 7.34 (dd, J=8.0, 4.7 Hz, 1H), 7.29 (d, J=8.3 Hz, 1H), 7.11 (dd, J=15.2, 4.9 Hz, 2H), 6.96 (d, J=8.9 Hz, 1H), 6.86 (dd, J=8.9, 2.6 Hz, 1H), 5.19 (s, 2H), 3.71 (s, 3H), 3.55 (s, 3H).

2. Synthesis of Compound 8-2e and 8-2f

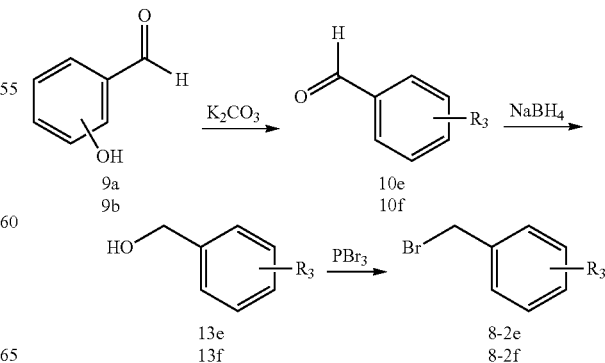

| Compound 8 | R₃ |
|---|---|
| 8-2e | 3-OCH₂CO₂C₂H₅ |
| 8-2f | 2-OCH₂C₆H₅ |

1.47 g (12 mmol, 1.0 eq) 3-hydroxybenzaldehyde (Compound 9b) was dissolved in 30 ml acetone, in the mixture was added 3.30 g (24 mmol, 2.0 eq) potassium carbonate and 1.34 ml (12 mmol, 1.0 eq) ethyl bromoacetate. After reacting for one night at room temperature, acetone was removed by vacuum distillation. Add water and EA (10 ml*2) to extract and wash the organic phase twice with saturated sodium chloride solution, then dry with anhydrous sodium sulfate and desolventizing to gain brown oily material. The crude product was then purified by column chromatography purification using mobile phase of PE:EA=6:1 to gain 1.50 g light yellow transparent oily material (Compound 10e). Compound 10f can be obtained with the same method from salicylaldehyde (compound 9a) and benzyl bromide.

Referring to reaction conditions of synthesizing compound 8-2a to 8-2d in application case 3, starting from Compound 10e and 10f to obtain compound 8-2e and 8-2f through sodium borohydride reduction and bromination reaction with phosphorus tribromide. The crude products were used without purification in the next step directly.

3. Synthesis of Scheme I-22 and I-26

| SchemeI | R₃ | Yield (%) |
|---|---|---|
| I-22 | 3-OCH₂CO₂C₂H₅ | 50.0 |
| I-26 | 2-OCH₂C₆H₅ | 40.3 |

Referring to reaction conditions of the fifth step of synthesizing scheme I-17 in Application case 1, starting from 2-hydroxy-N-(pyridin-3-yl) benzamide (Compound 7) and corresponding substituted benzyl bromides (compound 8-2e~8-20 to obtain scheme I-22 and I-26, that is: 2-(3-((2-(pyridin-3-ylcarbamoyl) phenoxy) methyl) phenoxy) acetate (Scheme I-22); 2-((2-benzyloxy) benzyloxy)-N-(pyridin-3-yl) benzamide (Scheme I-26).

The structures were confirmed correct and data are as follow:

Scheme I-22 MS(ESI) (m/z): 407.0 (M+H)⁺. ¹H NMR (400 MHz, DMSO-d₆)₆ ppm 11.11 (s, 1H), 9.27 (s, 1H), 8.61 (d, J=5.3 Hz, 1H), 8.54 (d, J=7.8 Hz, 1H), 7.97 (dd, J=8.5, 5.5 Hz, 1H), 7.64 (d, J=7.5 Hz, 1H), 7.53 (t, J=7.8 Hz, 1H), 7.26 (dt, J=10.4, 5.9 Hz, 2H), 7.13-7.04 (m, 3H), 6.82 (d, J=6.9 Hz, 1H), 5.21 (s, 2H), 4.71 (s, 2H), 4.11 (q, J=7.1 Hz, 2H), 1.16 (t, J=7.1 Hz, 3H).

Scheme I-26 MS(ESI) (m/z): 411.2 (M+H)⁺. ¹H NMR (400 MHz, DMSO-d₆)⁶ ppm 11.10 (s, 1H), 9.21 (s, 1H), 8.61 (d, J=5.1 Hz, 1H), 8.44 (d, J=8.5 Hz, 1H), 7.95 (dd, J=8.3, 5.5 Hz, 1H), 7.67 (d, J=7.4 Hz, 1H), 7.49 (dd, J=13.5, 7.0 Hz, 2H), 7.38 (d, J=7.2 Hz, 2H), 7.31-7.21 (m, 5H), 7.08 (t, J=8.3 Hz, 2H), 6.89 (t, J=7.4 Hz, 1H), 5.29 (s, 2H), 5.13 (s, 2H).

Application Case 4: Synthesis of Scheme I-27, I-28, I-29, I-30, I-31, I-32 and I-33

1. Synthesis of Compound 8-3a~8-3g

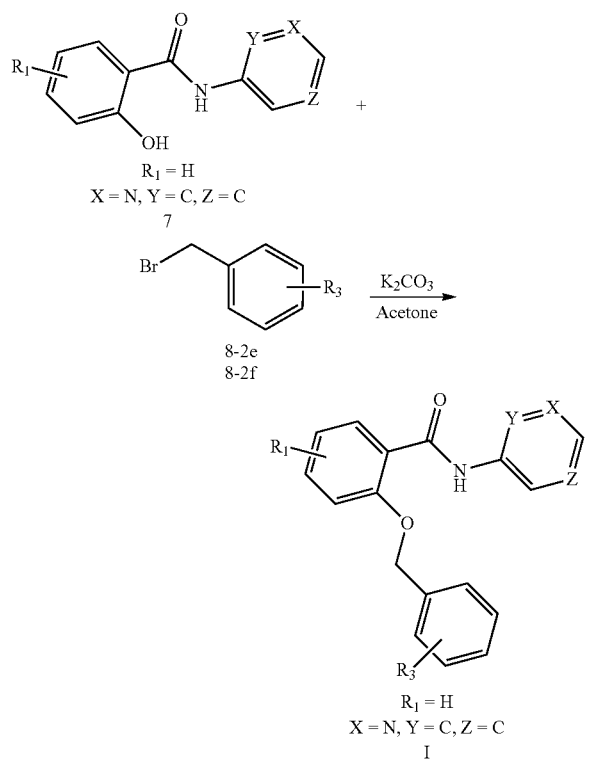

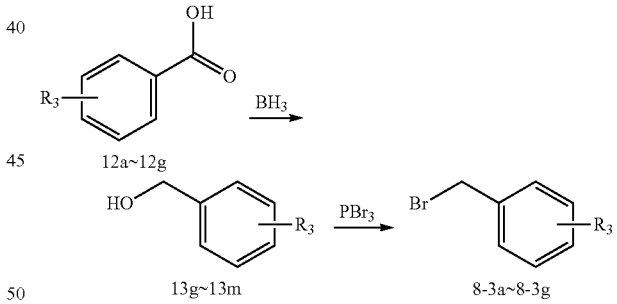

| Compound 8 | R₃ |
|---|---|
| 8-3a | 2-C₂H₅ |
| 8-3b | 4-C₂H₅ |
| 8-3c | 2,6-di-CH₃ |
| 8-3d | 2-OC₂H₅ |
| 8-3e | 2-OCH₃,5-Cl |
| 8-3f | 2-Cl,6-F |
| 8-3g | 2,5-di-Cl |

0.30 g (2 mmol, 1.0 eq) 2-ethyl-benzoic acid (compound 12a) was dissolved in 16 ml anhydrous THF, then 4 ml (4 mmol, 2.0 eq) 1M BH₃/THF solution was added dropwise under the condition of ice bath. After reacting at room temperature for 3.0 hours, THF was removed by vacuum distillation. 1 M HCl (aq) was added in the reaction system under the condition of ice water bath until no more air bubble came out. Then water and EA (10 ml*2) were added for extract and the organic phase was washed twice with saturated sodium bicarbonate solution and then twice with saturated sodium chloride solution. The solution was dried over anhydrous sodium sulfate and desolventlized to gain light yellow oily material (Compound 13g). The crude product was used without purification in the next step directly. Benzyl alcohol intermediate compound 13h to 13m can be obtained with the same reduction method from compound 12b to 12g.

Referring to the first reaction conditions of synthesizing compound 8-2a to 8-2d in application case 3, starting from compound 3g to 13m to obtain compound 8-3a to 8-3g through bromination reaction with phosphorus tribromide. The crude products were used without purification in the next step directly.

Synthesis of Scheme I-27, I-28, I-29, I-30, I-31, I-32 and I-33

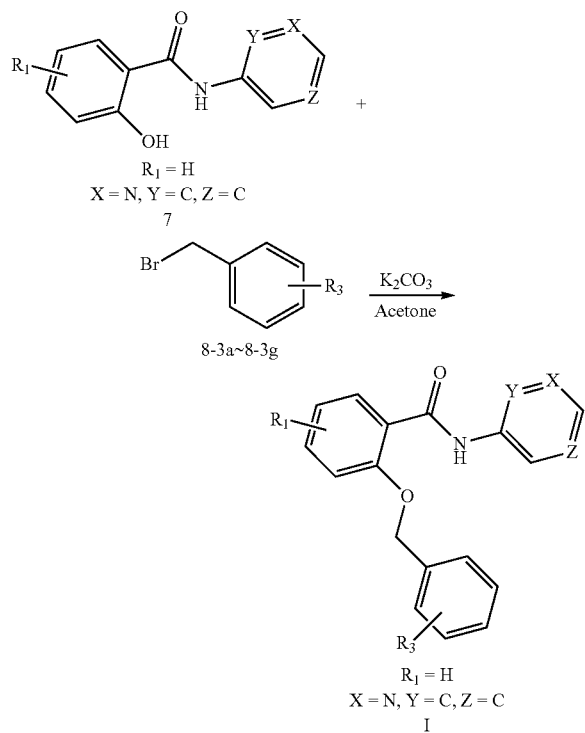

| Scheme I | $R_3$ | Yield (%) |
|---|---|---|
| I-27 | 2-$C_2H_5$ | 48.5 |
| I-28 | 4-$C_2H_5$ | 57.6 |
| I-29 | 2,6-di-$CH_3$ | 45.5 |
| I-30 | 2-$OC_2H_5$ | 22.9 |
| I-31 | 2-$OCH_3$,5-Cl | 48.6 |
| I-32 | 2-Cl,6-F | 74.0 |
| I-33 | 2,5-di-Cl | 73.0 |

Referring to reaction conditions of the fifth step of synthesizing scheme I-17 in Application case 1, starting from 2-hydroxy-N-(pyridin-3-yl) benzamide (compound 7) and corresponding substituted benzyl bromides (compound 8-3a~8-3g) to obtain scheme I-27 to I-33, that is: 2-((2-ethyl) benzyloxy)-N-(pyridin-3-yl) benzamide (Scheme I-27); 2-((4-ethyl) benzyloxy)-N-(pyridin-3-yl) benzamide (Scheme I-28); 2-((2,6-dimethyl) benzyloxy)-N-(pyridin-3-yl) benzamide (Scheme I-29); 2-((2-ethoxy) benzyloxy)-N-(pyridin-3-yl) benzamide (Scheme I-30); 2-((2-methoxy-5-chloro) benzyloxy)-N-(pyridin-3-yl) benzamide (Scheme I-31); 2-((2-chloro-6-fluoro) benzyloxy)-N-(pyridin-3-yl) benzamide (Scheme I-32); 2-((2,5-dichlorophenyl) benzyloxy)-N-(pyridin-3-yl) benzamide (Scheme I-33).

The structures were confirmed correct and data are as follow:

Scheme I-27 MS(ESI) (m/z): 333.0 (M+H)$^+$. $^1$H NMR (400 MHz, DMSO-d$_6$) δ ppm 11.06 (s, 1H), 9.18 (d, J=1.6 Hz, 1H), 8.60 (d, J=5.3 Hz, 1H), 8.44 (d, J=8.5 Hz, 1H), 7.94 (dd, J=8.5, 5.4 Hz, 1H), 7.64 (dd, J=7.6, 1.6 Hz, 1H), 7.61-7.55 (m, 1H), 7.49 (d, J=7.4 Hz, 1H), 7.40 (d, J=8.3 Hz, 1H), 7.26 (dt, J=13.9, 6.5 Hz, 2H), 7.19-7.10 (m, 2H), 5.27 (s, 2H), 2.68 (q, J=7.5 Hz, 2H), 1.12 (t, J=7.5 Hz, 3H).

Scheme I-28 m.p 164.8-167.1° C. MS(ESI) (m/z): 333.0 (M+H)$^+$. $^1$H NMR (400 MHz, DMSO-d$_6$) δ ppm 11.17 (s, 1H), 9.27 (s, 1H), 8.64 (d, J=5.3 Hz, 1H), 8.57 (d, J=8.6 Hz, 1H), 8.00 (dd, J=8.4, 5.6 Hz, 1H), 7.63 (d, J=6.7 Hz, 1H), 7.52 (t, J=7.8 Hz, 1H), 7.40 (d, J=7.8 Hz, 2H), 7.27 (d, J=8.4 Hz, 1H), 7.16 (d, J=7.8 Hz, 2H), 7.08 (t, J=7.5 Hz, 1H), 5.19 (s, 2H), 2.54 (q, J=7.5 Hz, 2H), 1.11 (t, J=7.6 Hz, 3H).

Scheme I-29 MS(ESI) (m/z): 333.1 (M+H)$^+$. $^1$H NMR (400 MHz, DMSO-d$_6$) δ ppm 11.07 (s, 1H), 9.08 (d, J=1.8 Hz, 1H), 8.57 (d, J=5.2 Hz, 1H), 8.30 (d, J=8.6 Hz, 1H), 7.91 (dd, J=8.5, 5.5 Hz, 1H), 7.58 (dd, J=13.8, 4.6 Hz, 2H), 7.45 (d, J=8.2 Hz, 1H), 7.11 (dd, J=13.3, 7.1 Hz, 2H), 7.00 (d, J=7.5 Hz, 2H), 5.18 (s, 2H), 2.31 (s, 6H). Scheme I-29 hydrochloride m.p 145.7-148.5° C.

Scheme I-30 MS(ESI) (m/z): 349.2 (M+H)$^+$. $^1$H NMR (400 MHz, DMSO-d$_6$)$^6$ ppm 10.34 (s, 1H), 8.53 (d, J=1.7 Hz, 1H), 8.25 (d, J=4.5 Hz, 1H), 8.03 (d, J=8.4 Hz, 1H), 7.77 (dd, J=7.6, 1.4 Hz, 1H), 7.57-7.47 (m, 2H), 7.32 (dd, J=12.9, 6.2 Hz, 3H), 7.10 (t, J=7.5 Hz, 1H), 7.02 (d, J=8.2 Hz, 1H), 6.90 (t, J=7.4 Hz, 1H), 5.24 (s, 2H), 3.99 (q, J=6.9 Hz, 2H), 1.20 (t, J=6.9 Hz, 3H).

Scheme I-31 m.p 119.0-122.8° C. MS(ESI) (m/z): 369.1 (M+H)$^+$. $^1$H NMR (400 MHz, DMSO-d$_6$) δ ppm 10.39 (s, 1H), 8.74 (d, J=2.2 Hz, 1H), 8.27 (dd, J=4.7, 1.3 Hz, 1H), 8.11 (ddd, J=8.3, 2.3, 1.5 Hz, 1H), 7.67 (dd, J=7.6, 1.6 Hz, 1H), 7.56-7.48 (m, 2H), 7.38-7.31 (m, 2H), 7.27 (d, J=8.3 Hz, 1H), 7.10 (t, J=7.5 Hz, 1H), 7.04 (d, J=8.8 Hz, 1H), 5.18 (s, 2H), 3.77 (s, 3H).

Scheme I-32 MS(ESI) (m/z): 357.0 (M+H)$^+$. $^1$H NMR (600 MHz, DMSO-d$_6$) δ ppm 10.87 (s, 1H), 9.11 (s, 1H), 8.57 (d, J=4.8 Hz, 1H), 8.38 (s, 1H), 7.90 (s, 1H), 7.66-7.58 (m, 2H), 7.50-7.44 (m, 2H), 7.36 (d, J=8.1 Hz, 1H), 7.28 (t, J=8.9 Hz, 1H), 7.17 (t, J=7.5 Hz, 1H), 5.33 (s, 2H). Scheme I-32 hydrochloride m.p 177.3-179.1° C.

Scheme I-33 MS(ESI) (m/z): 372.9 (M+H)$^+$. $^1$H NMR (600 MHz, DMSO-d$_6$) δ ppm 11.18-11.07 (m, 1H), 9.26 (s, 1H), 8.65-8.48 (m, 2H), 7.94 (d, J=4.7 Hz, 1H), 7.70-7.63 (m, 2H), 7.62-7.56 (m, 1H), 7.53 (d, J=8.5 Hz, 1H), 7.42 (dd, J=8.5, 2.5 Hz, 1H), 7.35 (d, J=8.3 Hz, 1H), 7.17 (t, J=7.5 Hz, 1H), 5.30 (s, 2H). Scheme I-33 hydrochloride m.p 185.0-186.9° C.

Application Case 5: Synthesis of Scheme I-34, I-35, I-36, I-37, I-38, I-39 and I-40

1. Synthesis of Compound 8-4a~8-4e

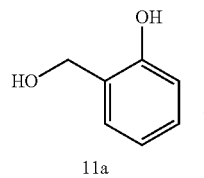

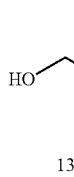

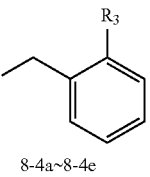

| Compound 8 | $R_3$ |
|---|---|
| 8-4a | 2-O(CH$_2$)$_4$Cl |
| 8-4b | 2-O(CH$_2$)$_5$Cl |
| 8-4c | 2-O(CH$_2$)$_6$Cl |
| 8-4d | 2-O(CH$_2$)$_5$CH$_3$ |
| 8-4e | 2-O(CH$_2$)$_6$CH$_3$ |

2.00 g (16 mmol, 1.0 eq) salicyl alcohol (compound 11a) was dissolved in 100 ml acetonitrile, to the mixture 5.20 g (37.6 mmol, 2.35 eq) potassium carbonate and 4.00 g (24 mmol, 1.5 eq) n-bromo-hexane was added. After reacting for 10 hours at 60° C., the solid was removed by vacuum filtration with the combined filtrate concentrated. The obtained crude product was then purified by column chromatography purification using mobile phase of PE:EA=25~9:1 to gain 1.80 g light yellow transparent oily material (Compound 13q), yield 54.1%. The crude product was used without purification in the next step directly. Compound 13n to 13p and compound 13r can be obtained with the same method from the reaction of 1-bromo-4-chlorobutane, 1-bromo-5-chloro pentane, 1-bromo-6-bromo-hexane, n-heptane with compound 11a.

Referring to the first reaction conditions of synthesizing compound 8-2a to 8-2d in application case 3, starting from Compound 13n to 13r to obtain compound 8-4a to 8-4e through bromination reaction with phosphorus tribromide. The crude products were used without purification in the next step directly.

2. Synthesis of Scheme I-34, I-35, I-36, I-37 and I-38

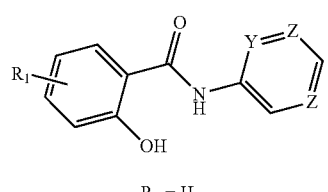

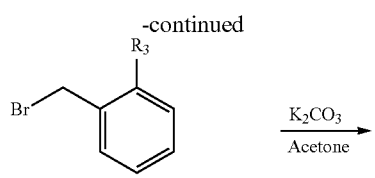

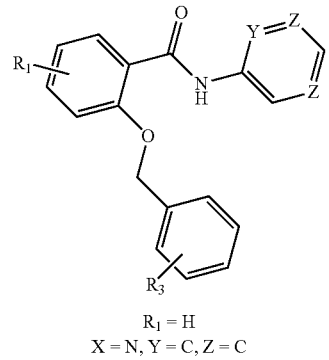

| Scheme I | $R_3$ | Yield (%) |
|---|---|---|
| I-34 | 2-O(CH$_2$)$_4$Cl | 60.0 |
| I-35 | 2-O(CH$_2$)$_5$Cl | 57.0 |
| I-36 | 2-O(CH$_2$)$_6$Cl | 61.0 |
| I-37 | 2-O(CH$_2$)$_5$CH$_3$ | 52.3 |
| I-38 | 2-O(CH$_2$)$_6$CH$_3$ | 57.1 |

Referring to reaction conditions of the fifth step of synthesizing scheme I-17 in Application case 1, starting from 2-hydroxy-N-(pyridin-3-yl) benzamide (compound 7) and corresponding substituted benzyl bromides (compound 8-4a~8-4e) to obtain scheme I-34 to I-38, that is: 2-(2-(4-chlorobutoxy) benzyloxy)-N-(pyridin-3-yl) benzamide (Scheme I-34); 2-(2-(5-chloro-pentoxy) benzyloxy)-N-(pyridin-3-yl) benzamide (Scheme I-35); 2-(2-(6-chloro-hexyloxy) benzyloxy)-N-(pyridin-3-yl) benzamide (Scheme I-36); 2-((2-hexyloxy) benzyloxy)-N-(pyridin-3-yl) benzamide (Scheme I-37); 2-((2-heptyloxy) benzyloxy)-N-(pyridin-3-yl) benzamide (Scheme I-38).

The structures were confirmed correct and data are as follow:

Scheme I-34 MS(ESI) (m/z): 411.0 (M+H)$^+$. $^1$H NMR (400 MHz, DMSO-d$_6$)$^6$ ppm 10.96 (s, 1H), 9.15 (d, J=1.8 Hz, 1H), 8.60 (d, J=5.1 Hz, 1H), 8.40 (d, J=8.7 Hz, 1H), 7.93 (dd, J=8.5, 5.4 Hz, 1H), 7.72 (dd, J=7.6, 1.7 Hz, 1H), 7.61-7.54 (m, 1H), 7.50-7.45 (m, 1H), 7.31 (dd, J=10.2, 5.0 Hz, 2H), 7.13 (t, J=7.3 Hz, 1H), 7.05 (d, J=8.1 Hz, 1H), 6.91 (t, J=7.3 Hz, 1H), 5.26 (s, 2H), 4.03 (t, J=5.7 Hz, 2H), 3.64 (t, J=6.1 Hz, 2H), 1.88-1.72 (m, 4H). Scheme I-34 hydrochloride m.p 127.4-128.1° C.

Scheme I-35 MS(ESI) (m/z): 425.0 (M+H)$^+$. $^1$H NMR (400 MHz, DMSO-d$_6$) δ ppm 10.95 (s, 1H), 9.14 (d, J=1.7 Hz, 1H), 8.60 (d, J=5.1 Hz, 1H), 8.39 (d, J=9.2 Hz, 1H), 7.93 (dd, J=8.5, 5.4 Hz, 1H), 7.73 (dd, J=7.6, 1.6 Hz, 1H), 7.61-7.54 (m, 1H), 7.47 (d, J=6.3 Hz, 1H), 7.32 (dd, J=10.7, 4.8 Hz, 2H), 7.14 (t, J=7.4 Hz, 1H), 7.05 (d, J=8.1 Hz, 1H), 6.91 (t, J=7.4 Hz, 1H), 5.26 (s, 2H), 3.99 (t, J=6.2 Hz, 2H), 3.58 (t, J=6.6 Hz, 2H), 1.76-1.62 (m, 4H), 1.52-1.42 (m, 2H).

Scheme I-36 MS(ESI) (m/z): 439.0 (M+H)$^+$. $^1$H NMR (400 MHz, DMSO-d$_6$) δ ppm 10.90-10.79 (m, 1H), 9.06 (d, J=12.3 Hz, 1H), 8.56 (d, J=5.2 Hz, 1H), 8.31 (d, J=8.5 Hz, 1H), 7.87 (t, J=9.5 Hz, 1H), 7.76 (d, J=7.6 Hz, 1H), 7.62-7.55 (m, 1H), 7.48 (d, J=7.4 Hz, 1H), 7.33 (t, J=7.1 Hz, 2H), 7.14 (t, J=7.5 Hz, 1H), 7.05 (d, J=8.3 Hz, 1H), 6.92 (t, J=7.4 Hz, 1H), 5.27 (s, 2H), 3.98 (t, J=6.3 Hz, 2H), 3.57 (t, J=6.6 Hz, 2H), 1.64 (dd, J=13.1, 6.5 Hz, 4H), 1.43-1.31 (m, 4H). Scheme I-36 hydrochloride m.p 113.7-115.4° C.

Scheme I-37 MS(ESI) (m/z): 405.0 (M+H)+. 1H NMR (400 MHz, DMSO-d6) δ ppm 11.04 (s, 1H), 9.18 (s, 1H), 8.62 (s, 1H), 8.42 (d, J=6.6 Hz, 1H), 7.97 (s, 1H), 7.71 (d, J=6.8 Hz, 1H), 7.60-7.42 (m, 2H), 7.25 (d, J=7.6 Hz, 2H), 7.17-6.83 (m, 3H), 5.22 (s, 2H), 3.92 (s, 2H), 1.59 (s, 2H), 1.27 (dd, J=17.1, 8.5 Hz, 2H), 1.18 (d, J=21.4 Hz, 4H), 0.76 (s, 3H).

Scheme I-38 MS(ESI) (m/z): 419.0 (M+H)+. 1H NMR (400 MHz, DMSO-d6) δ ppm 11.00 (s, 1H), 9.16 (s, 1H), 8.61 (d, J=5.1 Hz, 1H), 8.40 (d, J=8.4 Hz, 1H), 7.95 (dd, J=8.4, 5.5 Hz, 1H), 7.72 (dd, J=7.6, 1.4 Hz, 1H), 7.54 (t, J=7.1 Hz, 1H), 7.46 (d, J=6.8 Hz, 1H), 7.27 (t, J=7.7 Hz, 2H), 7.10 (t, J=7.4 Hz, 1H), 7.01 (d, J=8.2 Hz, 1H), 6.88 (t, J=7.4 Hz, 1H), 5.23 (s, 2H), 3.93 (t, J=6.3 Hz, 2H), 1.66-1.54 (m, 2H), 1.34-1.23 (m, 2H), 1.23-1.06 (m, 6H), 0.78 (t, J=6.9 Hz, 3H).

3. Synthesis of Compound 8-4f and 8-4g

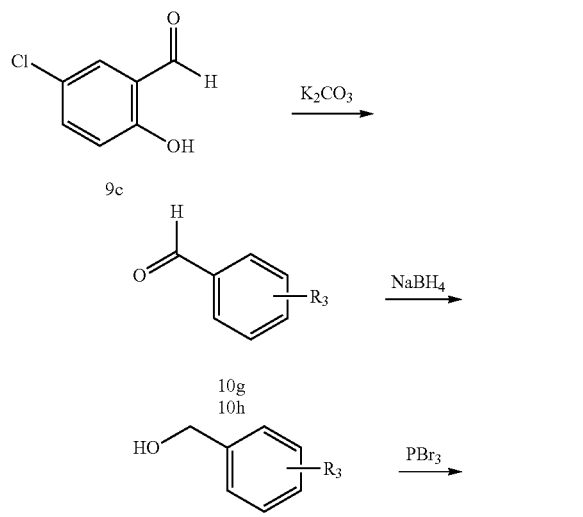

| Compound 8 | R3 |
|---|---|
| 8-4f | 2-O(CH2)5CH3,5-Cl |
| 8-4g | 2-O(CH2)6CH3,5-Cl |

4.70 g (30 mmol, 1.0 eq) 5-chloro-salicylaldehyde (compound 9c) was dissolved in 150 ml acetonitrile, in the mixture was added 10.35 g (75 mmol, 2.5 eq) potassium carbonate and 7.43 g (45 mmol, 1.5 eq) n-hexane bromine. After reacting for 10 hours at 60° C., the solid was removed by vacuum filtration with the combined filtrate concentrated and desolventizing to gain light yellow transparent oily material (compound 10g). Compound 10h was obtained with the same method from the reaction of n-bromo heptane with compound 9c. Referring to the third reaction conditions of synthesizing compound 8-2e and 8-2f in Application case 3, starting from compound 10g to 10h to obtain compound 8-4f to 8-4g through sodium borohydride reduction and bromination reaction with phosphorus tribromide. The crude products were used without purification in the next step directly.

4. Synthesis of Scheme I-39 and I-40

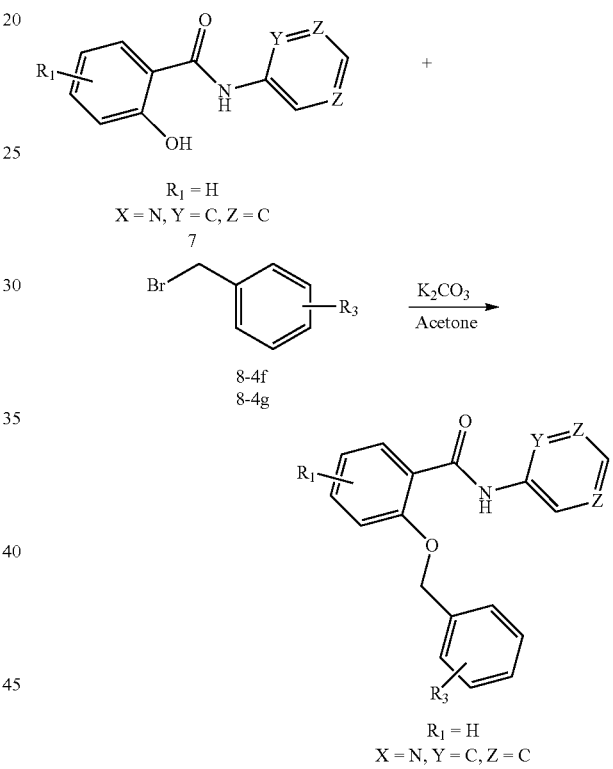

| Scheme I | R3 | Yield (%) |
|---|---|---|
| I-39 | 2-O(CH2)5CH3,5-Cl | 45.5 |
| I-40 | 2-O(CH2)6CH3,5-Cl | 51.1 |

Referring to reaction conditions of the fifth step of synthesizing scheme I-17 in Application case 1, starting from 2-hydroxy-N-(pyridin-3-yl) benzamide (Compound 7) and corresponding substituted benzyl bromides (compound 8-4f and 8-4g) to obtain scheme I-39 and I-40, that is: 2-((5-chloro-2-methoxy) benzyloxy)-N-(pyridin-3-yl) benzamide (Scheme I-39); 2-((5-chloro-2-oxo-heptyl yl) benzyloxy)-N-(pyridin-3-yl) benzamide (Scheme I-40).

The structures were confirmed correct and data are as follow: Scheme I-39 MS(ESI) (m/z): 439.2 (M+H)+. 1H NMR (400 MHz, DMSO-d6) δ ppm 11.18 (s, 1H), 9.27 (d, J=1.8 Hz, 1H), 8.64 (d, J=5.4 Hz, 1H), 8.56 (d, J=8.7 Hz, 1H), 8.00 (dd, J=8.6, 5.5 Hz, 1H), 7.65 (dd, J=7.6, 1.5 Hz, 1H), 7.58-7.51 (m, 1H), 7.45 (d, J=2.6 Hz, 1H), 7.26 (dd, J=12.2, 5.7 Hz, 2H), 7.11 (t, J=7.5 Hz, 1H), 7.02 (d, J=8.8 Hz, 1H), 5.17 (s, 2H), 3.95 (t, J=6.4 Hz, 2H), 1.68-1.58 (m, 2H), 1.32 (dd, J=14.4, 7.1 Hz, 2H), 1.22 (dt, J=7.1, 4.7 Hz, 4H), 0.80 (t, J=7.0 Hz, 3H). Scheme I-39 hydrochloride m.p 155.3-158.0° C.

Scheme I-40 MS(ESI) (m/z): 453.3 (M+H)$^+$. $^1$H NMR (400 MHz, DMSO-d$_6$)$_6$ ppm 11.16 (s, 1H), 9.26 (d, J=2.0 Hz, 1H), 8.64 (d, J=5.3 Hz, 1H), 8.54 (d, J=8.7 Hz, 1H), 7.99 (dd, J=8.6, 5.5 Hz, 1H), 7.66 (dd, J=7.6, 1.6 Hz, 1H), 7.58-7.52 (m, 1H), 7.46 (d, J=2.6 Hz, 1H), 7.26 (dd, J=12.4, 5.8 Hz, 2H), 7.12 (t, J=7.5 Hz, 1H), 7.02 (d, J=8.9 Hz, 1H), 5.17 (s, 2H), 3.95 (t, J=6.4 Hz, 2H), 1.69-1.57 (m, 2H), 1.38-1.28 (m, 2H), 1.27-1.11 (m, 6H), 0.80 (t, J=6.9 Hz, 3H). I-40 hydrochloride m.p 156.9-159.2° C.

Application Case 6: Synthesis of Scheme I-41, I-42, I-43, I-44 and I-45

1. Synthesis of Compound 13u

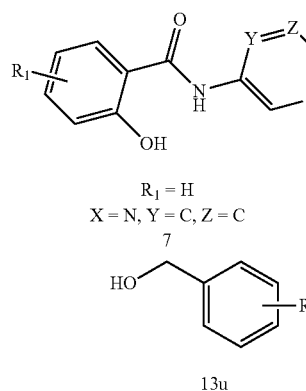

Referring to the first reaction conditions of synthesizing compound 13a to 13d in Application case 3, starting from Compound 10i to obtain compound 13u through sodium borohydride reduction. The crude product was used without purification in the next step directly.

2. Synthesis of Scheme I-41

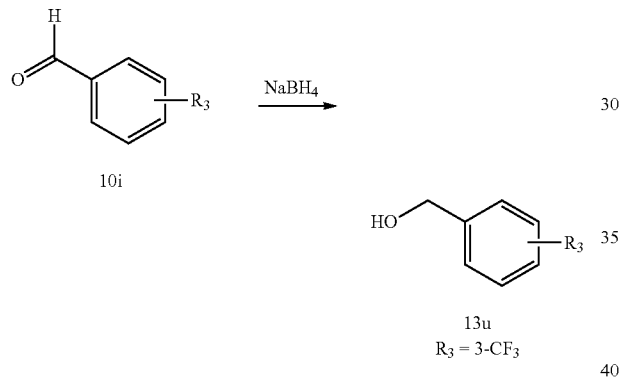

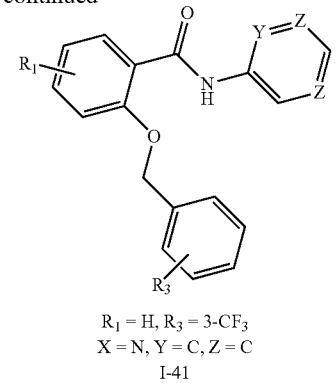

0.20 g (0.75 mmol, 1.5 eq) Ph$_3$P and 0.12 ml (0.75 mmol, 1.5 eq) DEAD were dissolved in 10 ml anhydrous THF, to the mixture 5 ml THF solution of 0.11 g (0.5 mmol, 1.0 eq) 2-hydroxy-N-(pyridin-3-yl) benzamide (compound 7) was added dropwise under the condition of ice bath, followed 5 ml THF solution of 0.10 g (0.55 mmol, 1.1 eq) compound 13u was added. After reacting for 2.0 hours, THF was removed by vacuum distillation. To the residue, 10 ml water and 15 ml EA were added. After the pH of the solution was adjusted to 2 with dilute hydrochloric, the EA layer was separated, and the aqueous layer was neutralized to pH=8~9 with NaOH (aq). The precipitated solid was filtered to give a white powdery solid crude product. The crude product was then purified by column chromatography purification using mobile phase of PE:EA=2:1 to gain 0.04 g white powdery solid, yield 21.5%.

The structure is confirmed correct and data are as follow: Scheme I-41 m.p 70.2-72.9° C. MS(ESI) (m/z): 373.0 (M+H)$^+$. $^1$H NMR (400 MHz, DMSO-d$_6$) δ ppm 10.41 (s, 1H), 8.75 (d, J=2.3 Hz, 1H), 8.25 (dd, J=4.7, 1.4 Hz, 1H), 8.09 (ddd, J=8.3, 2.4, 1.5 Hz, 1H), 7.91 (s, 1H), 7.79 (d, J=7.6 Hz, 1H), 7.68-7.49 (m, 4H), 7.36-7.26 (m, 2H), 7.13-7.07 (m, 1H), 5.31 (s, 2H).

3. Synthesis of Scheme I-42, I-43 and I-44

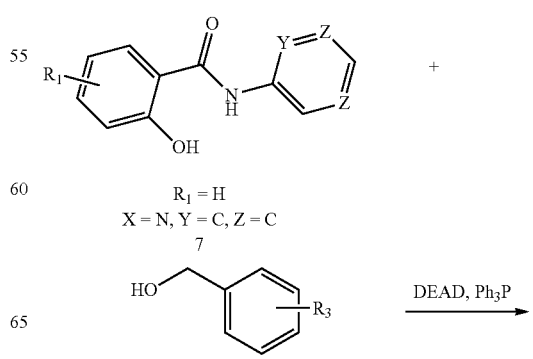

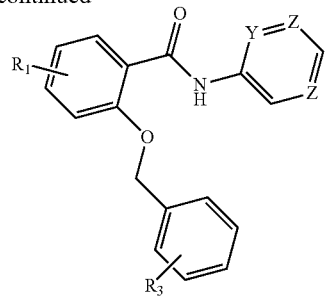

R₁ = H
X = N, Y = C, Z = C
I

| Scheme I | R₃ | Yield (%) |
|---|---|---|
| I-42 | 2-CF₃ | 43.0 |
| I-43 | 2-CH₃,5-Cl | 39.0 |
| I-44 | 2-CH₃,3-Cl | 28.4 |

Referring to reaction conditions of the second step of synthesizing scheme I-41 in Application case 6, starting from 2-hydroxy-N-(pyridin-3-yl) benzamide (compound 7) and corresponding substituted benzyl alcohols to obtain scheme I-42 to I-44, that is: 2-((2-trifluoromethyl) benzyloxy)-N-(pyridin-3-yl) benzamide (Scheme I-42); 2-((2-methyl 5-chloro-yl) benzyloxy)-N-(pyridin-3-yl) benzamide (Scheme I-43); 2-((2-methyl-3-chloro) benzyloxy)-N-(pyridin-3-yl) benzamide (Scheme I-44).

The structures were confirmed correct and data are as follow:

Scheme I-42 m.p 73.6-75.1° C. MS(ESI) (m/z): 373.0 (M+H)⁺. ¹H NMR (400 MHz, DMSO-d₆) δ ppm 10.37 (s, 1H), 8.67 (d, J=2.4 Hz, 1H), 8.28 (dd, J=4.7, 1.4 Hz, 1H), 8.13-8.07 (m, 1H), 7.88 (d, J=7.6 Hz, 1H), 7.79 (d, J=7.6 Hz, 1H), 7.71-7.61 (m, 2H), 7.61-7.52 (m, 2H), 7.36 (dd, J=8.3, 4.7 Hz, 1H), 7.27 (d, J=8.3 Hz, 1H), 7.14 (t, J=7.4 Hz, 1H), 5.40 (s, 2H).

Scheme I-43 MS(ESI) (m/z): 353.0 (M+H)⁺. ¹H NMR (400 MHz, DMSO-d₆) δ ppm 11.20 (s, 1H), 9.26 (s, 1H), 8.62 (d, J=5.3 Hz, 1H), 8.54 (d, J=8.6 Hz, 1H), 7.97 (dd, J=8.5, 5.5 Hz, 1H), 7.60 (d, J=7.6 Hz, 1H), 7.55 (d, J=7.4 Hz, 1H), 7.47 (s, 1H), 7.36 (d, J=8.4 Hz, 1H), 7.24-7.17 (m, 2H), 7.12 (t, J=7.5 Hz, 1H), 5.20 (s, 2H), 2.27 (s, 3H). Scheme I-43 hydrochloride m.p 177.8-178.9° C.

Scheme I-44 m.p 98.6-100.5° C. MS(ESI) (m/z): 353.1 (M+H)⁺. ¹H NMR (400 MHz, DMSO-d₆) δ ppm 10.37 (s, 1H), 9.00 (s, 1H), 8.66 (d, J=1.9 Hz, 1H), 8.26 (d, J=4.1 Hz, 1H), 8.07 (d, J=8.7 Hz, 1H), 7.64-7.57 (m, 2H), 7.39 (d, J=7.9 Hz, 1H), 7.37-7.31 (m, 2H), 7.15 (t, J=7.8 Hz, 1H), 7.09 (t, J=7.4 Hz, 1H), 5.27 (s, 2H), 2.33 (s, 3H).

4. Synthesis of Scheme I-45

Referring to reaction conditions of the second step of synthesizing scheme I-41 in Application case 6, starting from 2-hydroxy-N-(pyridin-3-yl) benzamide (compound 7) and 1-naphthyl methanol to obtain 2-((naphthalen-1-yl) methoxy)-N-(pyridin-3-yl) benzamide (Scheme I-45).

The structures were confirmed correct and data are as follow: Scheme I-45 m.p 91.4-93.9° C. MS(ESI) (m/z): 355.1 (M+H)⁺. ¹H NMR (400 MHz, DMSO-d₆) ppm 10.23 (s, 1H), 8.99 (s, 1H), 8.31 (d, J=2.3, 1H), 8.25-8.14 (m, 2H), 7.95 (dd, J=13.3, 5.3, 2H), 7.84-7.78 (m, 1H), 7.75-7.68 (m, 2H), 7.64-7.43 (m, 4H), 7.23 (dd, J=8.3, 4.7, 1H), 7.13 (t, J=7.4, 1H), 5.72 (s, 2H).

Application Case 7: Synthesis of Scheme I-46, I-47 and I-48

1. Synthesis of Scheme I-46 and I-48

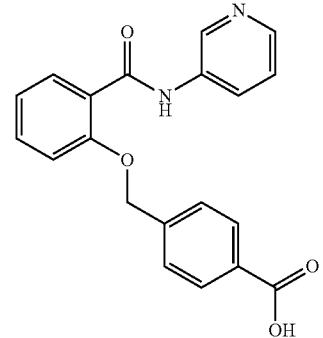

0.63 g (1.67 mmol, 1.0 eq) scheme I-19 was dissolved in 7.5 ml methanol, in the mixture 7.5 ml LiOH (aq, 0.45 mol/L) was added slowly in ice water bath. After reacting for 12 hours at room temperature, methanol was removed by vacuum distillation. 1 mol/L HCl(aq) was added to the remaining matter to regulate system pH to 2~3. The precipitated solid was filtered and dried to give a white powdery solid (scheme I-46) of 0.49 g, yield 84.5%.

The structures were confirmed correct and data are as follow: m.p. 256.6-258.0° C. MS (ESI) (m/z): 349.0 (M+H)⁺. 347.0 (M−H)⁻. ¹H NMR (400 MHz, DMSO-d₆) δ ppm 12.98 (s, 1H), 10.40 (s, 1H), 8.76 (d, J=2.1 Hz, 1H), 8.29 (dd, J=4.7, 1.2 Hz, 1H), 8.16 (d, J=8.4 Hz, 1H), 7.92 (d, J=8.2 Hz, 2H), 7.74-7.59 (m, 3H), 7.58-7.46 (m, 1H), 7.38 (dd, J=8.3, 4.7 Hz, 1H), 7.28 (d, J=8.3 Hz, 1H), 7.12 (t, J=7.4 Hz, 1H), 5.34 (s, 2H).

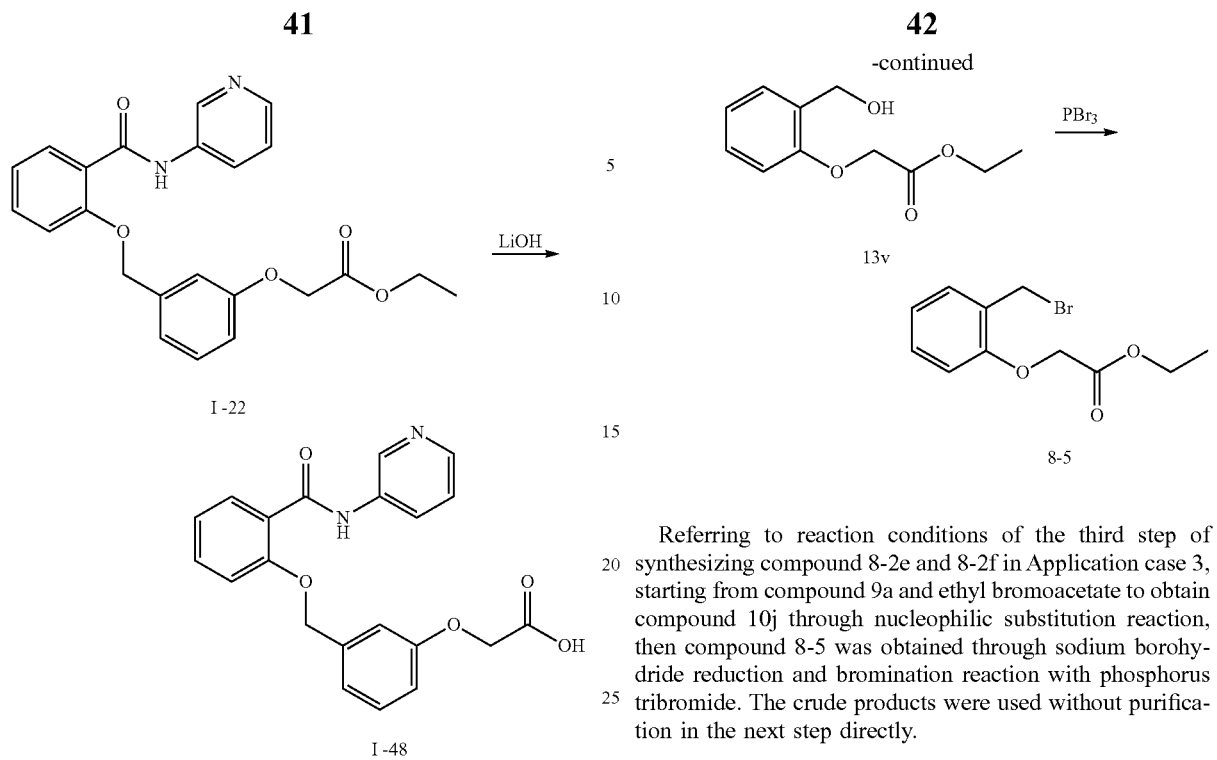

0.20 g (0.49 mmol, 1.0 eq) scheme I-22 was dissolved in 3.0 ml methanol, in the mixture 3.0 ml LiOH (aq, 0.45 mol/L) was added slowly in ice water bath. After reacting for 0.5 hours at room temperature, methanol was removed by vacuum distillation. 1 mol/L HCl(aq) was added to the remain matter to regulate system pH to 3~4. The precipitated solid was filtered and dried to give a white powdery solid (scheme I-48) of 0.10 g, yield 53.8%.

The structures were confirmed correct and data are as follow: m.p 203.6-205.9° C. MS(ESI) (m/z): 379.0 (M+H)$^+$. $^1$H NMR (400 MHz, DMSO-d$_6$) δ ppm 10.42 (s, 1H), 8.79 (s, 1H), 8.28 (s, 1H), 8.10 (d, J=7.3 Hz, 1H), 7.67 (d, J=6.9 Hz, 1H), 7.50 (d, J=7.1 Hz, 1H), 7.37 (s, 1H), 7.26 (d, J=5.8 Hz, 2H), 7.18-7.02 (m, 3H), 6.85 (d, J=7.4 Hz, 1H), 5.20 (s, 2H), 4.63 (s, 2H).

2. Synthesis of Scheme I-47

Referring to reaction conditions of the third step of synthesizing compound 8-2e and 8-2f in Application case 3, starting from compound 9a and ethyl bromoacetate to obtain compound 10j through nucleophilic substitution reaction, then compound 8-5 was obtained through sodium borohydride reduction and bromination reaction with phosphorus tribromide. The crude products were used without purification in the next step directly.

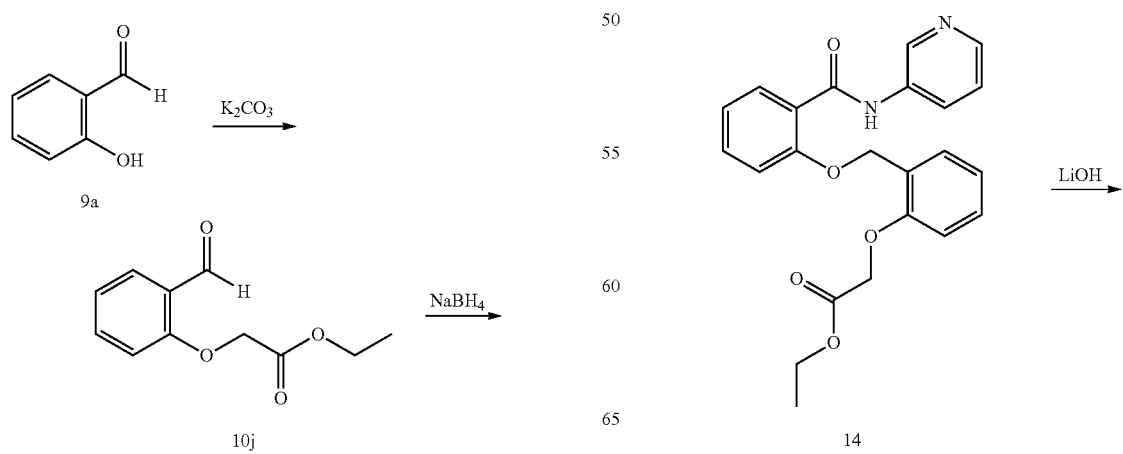

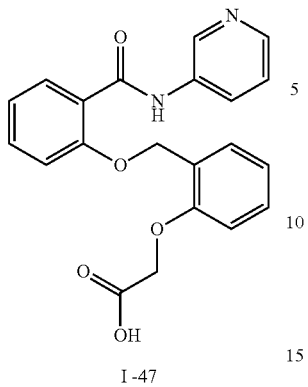

I-47

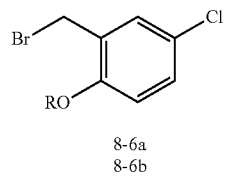

8-6a
8-6b

| Compound 8 | R |
|---|---|
| 8-6a | —(CH$_2$)$_3$OCH$_3$ |
| 8-6b | —(CH$_2$)$_2$OCH$_3$ |

Referring to reaction conditions of the fifth step of synthesizing scheme I-17 in Application case 1, starting from 2-hydroxy-N-(pyridin-3-yl) benzamide (Compound 7) and substituted benzyl bromide (compound 8-5) obtained above to obtain compound 14. Then refer to reaction conditions of the first step of synthesizing scheme I-48 in Application case 7, compound 14 was LiOH hydrolyzed to obtain scheme I-47.

The structures were confirmed correct and data are as follow: m.p 179.9-183.8° C. MS(ESI) (m/z): 379.0 (M+H)$^+$. $^1$H NMR (400 MHz, DMSO-d$_6$) δ ppm 13.14 (s, 1H), 10.62 (s, 1H), 8.89 (d, J=1.9 Hz, 1H), 8.43 (dd, J=5.0, 1.1 Hz, 1H), 8.22 (d, J=8.4 Hz, 1H), 7.74 (dd, J=7.6, 1.7 Hz, 1H), 7.62 (dd, J=8.4, 5.0 Hz, 1H), 7.59-7.48 (m, 2H), 7.36-7.28 (m, 2H), 7.13 (t, J=7.5 Hz, 1H), 7.00 (d, J=8.2 Hz, 1H), 6.94 (t, J=7.4 Hz, 1H), 5.33 (s, 2H), 4.77 (s, 2H).

Application Case 8: Synthesis of Scheme I-49, I-50 and I-51

1. Synthesis of Compound 8-6a and 8-6b

Referring to the reaction conditions of the first step to synthesize compound 13a to 13d in Application case 3, starting from Compound 9c to obtain compound 11b through sodium borohydride reduction.

0.48 g (3 mmol, 1.0 eq) 4-chloro-2-(hydroxymethyl) phenol (compound 11b) obtained above was dissolved in 7.5 ml DMF. In the mixture were added 2.49 g (18 mmol, 6.0 eq) potassium carbonate and 2.75 g (18 mmol, 6.0 eq) bromo-3-methoxy propane. After reacting 10 hours at 100° C., 20 ml water and 15 ml*2 EA were added for extract. The organic phase was washed twice with saturated sodium chloride solution, dried over anhydrous sodium sulfate and desolventized to gain yellow transparent oily crude product. The crude product was then purified by column chromatography purification using mobile phase of PE:EA=10:1 to gain 0.33 g light yellow transparent oily product (compound 13w), yield 48%. Compound 13x was obtained from compound 11b and 1-bromo-2-methoxy ethane with the reaction mentioned above.

Referring to reaction conditions of the first step of synthesizing compound 8-4a to 8-4e in Application case 5, compound 8-6a and 8-6b were obtained from compound 13w and 13x through bromination reaction with phosphorus tribromide. The crude products were used without purification in the next step directly.

2. Synthesis of Scheme I-49 and I-50

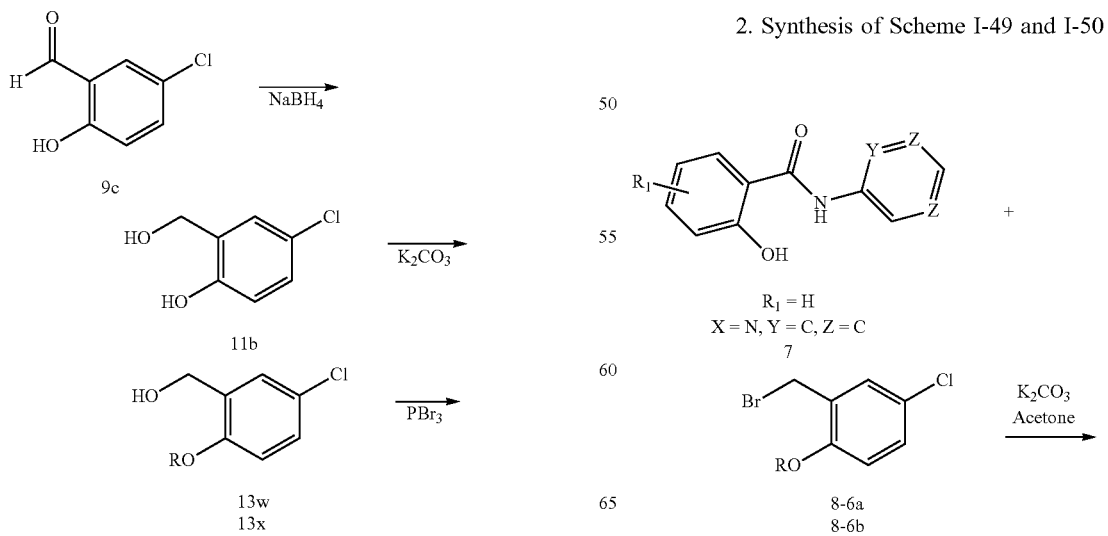

-continued

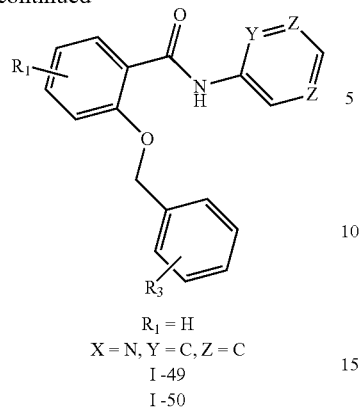

R₁ = H
X = N, Y = C, Z = C
I-49
I-50

| SchemeI | R₃ | Yield (%) |
|---|---|---|
| I-49 | 2-O(CH₂)₃OCH₃,5-Cl | 82.8 |
| I-50 | 2-O(CH₂)₂OCH₃,5-Cl | 39.4 |

Referring to reaction conditions of the fifth step of synthesizing scheme I-17 in Application case 1, starting from 2-hydroxy-N-(pyridin-3-yl) benzamide (Compound 7) and corresponding substituted benzyl bromides (compound 8-6a and 8-6b) to obtain scheme I-49 and I-50, that is: 2-((5-chloro-2-(3-methoxy-propoxy)) benzyloxy)-N-(pyridin-3-yl) benzamide (Scheme I-49); 2-((5-chloro-2-(2-methoxy-ethoxy)) benzyloxy)-N-(pyridin-3-yl) benzamide (Scheme I-50).

The structures were confirmed correct and data are as follow:

Scheme I-49 MS(ESI) (m/z): 427.0 (M+H)⁺. ¹H NMR (400 MHz, DMSO-d₆) δ ppm 10.36 (s, 1H), 8.67 (d, J=2.3 Hz, 1H), 8.26 (dd, J=4.7, 1.4 Hz, 1H), 8.12-8.06 (m, 1H), 7.70 (dd, J=7.6, 1.7 Hz, 1H), 7.53 (dd, J=12.3, 2.2 Hz, 2H), 7.37-7.30 (m, 2H), 7.28 (d, J=8.3 Hz, 1H), 7.11 (t, J=7.4 Hz, 1H), 7.05 (d, J=8.8 Hz, 1H), 5.19 (s, 2H), 4.01 (t, J=6.2 Hz, 2H), 3.36 (t, J=6.2 Hz, 2H), 3.13 (s, 3H), 1.87 (p, J=6.2 Hz, 2H).

Scheme I-50 MS(ESI) (m/z): 413.0 (M+H)⁺. ¹H NMR (400 MHz, DMSO-d₆)⁶ ppm 10.35 (s, 1H), 8.71 (d, J=2.3 Hz, 1H), 8.27 (dd, J=4.7, 1.4 Hz, 1H), 8.10 (ddd, J=8.3, 2.4, 1.5 Hz, 1H), 7.69 (dd, J=7.6, 1.7 Hz, 1H), 7.55 (d, J=2.5 Hz, 1H), 7.53-7.49 (m, 1H), 7.37-7.34 (m, 1H), 7.32 (dd, J=8.9, 2.6 Hz, 1H), 7.25 (d, J=8.3 Hz, 1H), 7.12 (d, J=7.5 Hz, 1H), 7.07 (d, J=8.9 Hz, 1H), 5.19 (s, 2H), 4.11 (t, J=4.4 Hz, 2H), 3.59 (t, J=4.4 Hz, 2H), 3.21 (s, 3H).

3. Synthesis of Scheme I-51

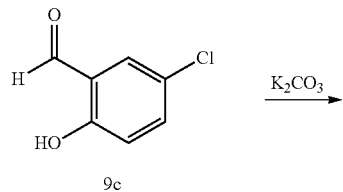

9c

-continued

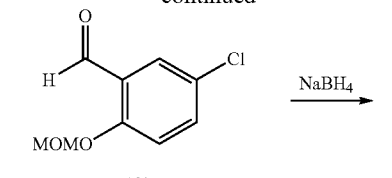

10k

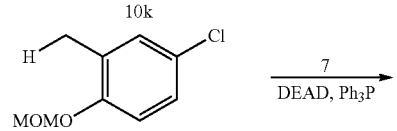

13y

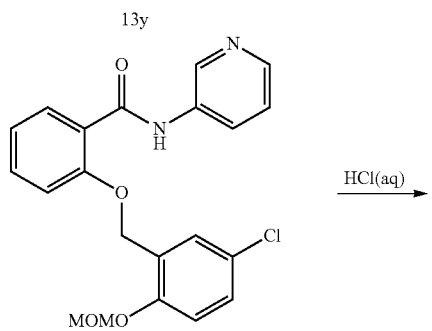

15

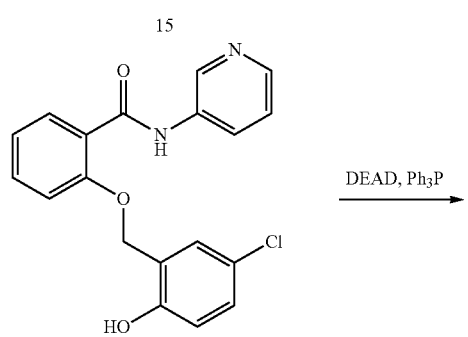

16

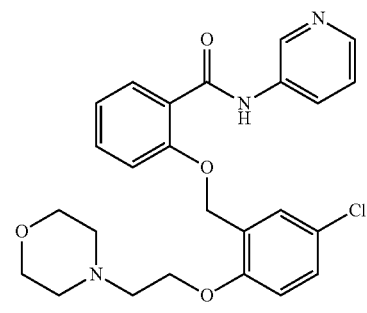

I-51

3.14 g (20 mmol, 1.0 eq) 5-chloro-2-hydroxybenzaldehyde (Compound 9c) was dissolved in 100 ml acetone. In the mixture were added 11.0 g (80 mmol, 4.0 eq) potassium carbonate and 3.62 ml (48 mmol, 2.4 eq) methoxymethyl chloride (MOMCl). After reacting for 1.0 hour at 30° C., acetone was removed by vacuum distillation and the crude product was then purified by column chromatography purification using mobile phase of PE:EA=25:1 to gain 1.50 g colorless transparent oily product (compound 10k), yield 37.3%.

Using the reaction conditions of the third step of synthesizing compound 8-2e and 8-2f in Application case 3, compound 13y was obtained from compound 10k through sodium borohydride reduction. The crude products were used without purification in the next step directly.

0.80 g (3.0 mmol, 1.5 eq) Ph₃P and 0.48 ml (3.0 mmol, 1.5 eq) DEAD were dissolved in 20 ml anhydrous THF. To the mixture was added 10 ml THF solution of 0.43 g (2.0 mmol, 1.0 eq) 2-hydroxy-N-(pyridin-3-yl) benzamide (compound 7) dropwise under the condition of ice bath, then 10 ml THF solution of 0.41 g (2.0 mmol, 1.0 eq) compound 13y. After reacting for 2.0 hours at room temperature, THF was removed by vacuum distillation. The brown oily crude product was then purified by column chromatography purification using mobile phase of PE:EA=2:1 to gain 0.74 g white solid (compound 15), yield 92.5%.

0.53 g (1.32 mmol, 1.0 eq) compound 15 was dissolved in 24 ml methanol. To the mixture was added 0.24 ml HCl (con) dropwise under the condition of ice water bath. After reacting for 10 hours at 55° C., methanol was removed by vacuum distillation to gain 0.39 g white solid (compound 16), yield 83.0%.

0.13 g (0.50 mmol, 1.5 eq) Ph₃P and 0.08 ml (0.50 mmol, 1.5 eq) DEAD were dissolved in 2 ml anhydrous THF. To the mixture was added 1 ml THF solution of 0.12 g (0.33 mmol, 1.0 eq) compound 16 dropwise under the condition of ice bath, then 1 ml THF solution of 0.04 g (0.33 mmol, 1.0 eq) 2-morpholino ethanol was added. After reacting for 2.0 hours at room temperature, THF was removed by vacuum distillation. The yellow oily crude product was then purified by column chromatography purification using mobile phase of PE:EA=1:1 to gain 0.04 g white waxy solid (Scheme I-51), yield 25.3%.

The structure was confirmed correct and data are as follow:

Scheme I-51 MS(ESI) (m/z): 468.0 (M+H)⁺. ¹H NMR (400 MHz, CDCl₃) δ ppm 10.02 (s, 1H), 8.32-8.18 (m, 3H), 8.09 (s, 1H), 7.58-7.48 (m, 1H), 7.47-7.30 (m, 2H), 7.25-7.21 (m, 1H), 7.15 (dd, J=16.4, 8.1 Hz, 2H), 6.98 (d, J=8.7 Hz, 1H), 5.20 (s, 2H), 4.08 (t, J=5.6 Hz, 2H), 3.54-3.43 (m, 4H), 2.60 (t, J=5.6 Hz, 2H), 2.38-2.26 (m, 4H).

Application Case 9: Synthesis of Scheme I-52 and I-53

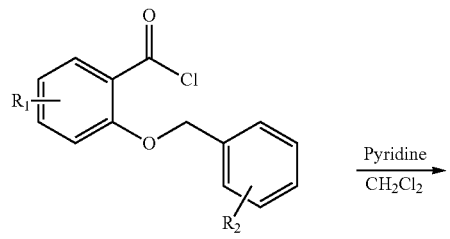

R₁ = H, R₂ = H
5a

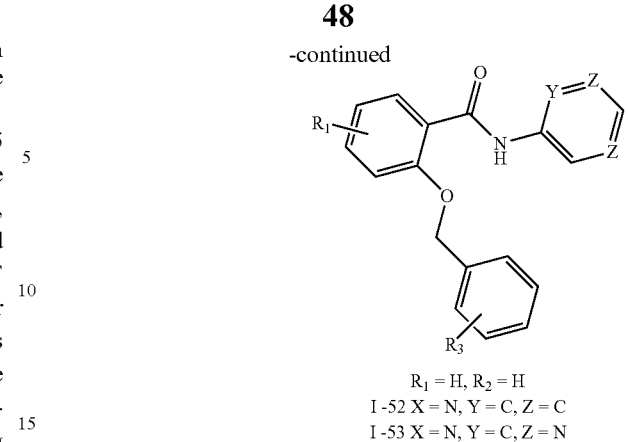

R₁ = H, R₂ = H
I-52 X = N, Y = C, Z = C
I-53 X = N, Y = C, Z = N

Referring to reaction conditions of the third step of synthesizing compound 6a from compound 5a in Application case 1, starting from Compound 5a and 2-aminopyridine and 5-amino-pyrimidine individually to obtain scheme I-52 and I-53, that is: 2-benzyloxy-N-(pyridin-2-yl) benzamide (Scheme I-52); 2-benzyloxy-N-(pyrimidin-5-yl) benzamide (Scheme I-53).

The structures were confirmed correct and data are as follow:

Scheme I-52 m.p 112.3-114.9° C. MS(ESI) (m/z): 305.2 (M+H)⁺. ¹H NMR (400 MHz, DMSO-d₆) δ ppm 10.58 (s, 1H), 8.30 (dd, J=4.8, 1.0 Hz, 1H), 8.22 (d, J=8.3 Hz, 1H), 7.86 (dd, J=7.7, 1.7 Hz, 1H), 7.84-7.77 (m, 1H), 7.53 (dd, J=13.9, 4.5 Hz, 3H), 7.39-7.28 (m, 4H), 7.12 (dt, J=12.3, 4.1 Hz, 2H), 5.34 (s, 2H).

Scheme I-53 m.p 145.3-148.9° C. MS(ESI) (m/z): 306.0 (M+H)⁺. ¹H NMR (400 MHz, DMSO-d₆) δ ppm 10.53 (s, 1H), 9.00 (s, 2H), 8.88 (s, 1H), 7.68 (dd, J=7.6, 1.6, 1H), 7.57-7.45 (m, 3H), 7.33 (ddd, J=16.5, 10.5, 5.3, 4H), 7.10 (t, J=7.5, 1H), 5.24 (s, 2H).

Application Case 10: Synthesis of Scheme I-54, I-55, I-56, I-57, I-58, I-59 and I-60

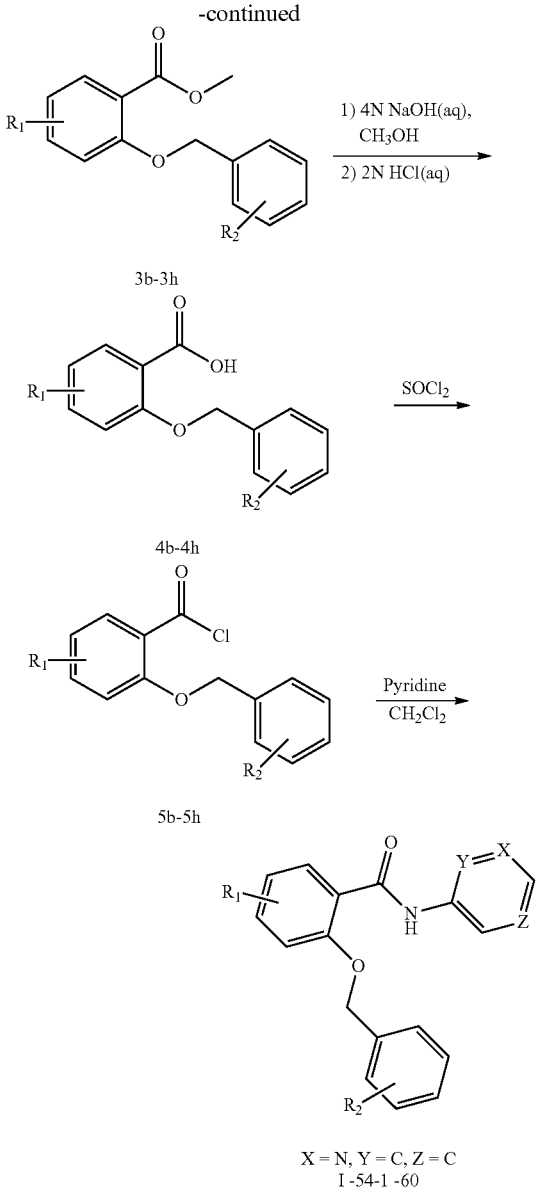

| Scheme I | $R_1$ | $R_2$ |
|---|---|---|
| Scheme I-54 | 5-Cl | 2,6-di-Cl |
| Scheme I-55 | 5-Cl | 2-Cl,5-F |
| Scheme I-56 | 4-Cl | 2-Cl |
| Scheme I-57 | 5-$NO_2$ | 2-Cl |
| Scheme I-58 | 4-Br | 2-Cl |
| Scheme I-59 | 5-$OCH_3$ | 2-Cl |
| Scheme I-60 | 4-$OCH_3$ | 2-Cl |

0.86 g (5 mmol, 1.0 eq) 5-chloro-salicylic acid (compound 1a) was dissolved in 7 ml methanol. To the mixture was added 0.90 g (7 mmol, 1.4 eq) thionyl chloride under the condition of ice bath. After the reaction was refluxed for 7.0 hours, it is cooled to room temperature. The methanol was removed to obtain 0.90 g pale yellow oily crude product (compound 2b), which was used without purification in the next step directly. According to this method, compound 2c to 2f were obtained from 4-chloro-salicylate (compound 1b), 5-nitro-salicylic acid (compound 1c), 4-bromo acid (compound 1d) and 5-methoxy-salicylic acid (compound 1e).

Referring to the first reaction condition of synthesizing compound 3a from compound 2a in application case 1, starting from compound 2b to 2f obtained above and commercially available 4-methoxy methyl salicylate (compound 2g) together with substituted benzyl bromides can obtain compound 3d to 3h. Referring to the second reaction from compound 3a to compound 4a in application case 1, compound 4b to 4h can be obtained through hydrolysis of compound 3b to 3h. Then referring to the third reaction from compound 4a to compound 6a in application case 1, scheme I-54 to I-60 can be obtained from compound 4b to 4h through acylating chlorination and amidation, that is: 5-chloro-2-((2,6-dichlorophenyl) benzyloxy)-N-(pyridin-3-yl) benzamide (Scheme I-54); 5-Chloro-2-((2-chloro 5-fluoro) benzyloxy)-N-(pyridin-3-yl) benzamide (Scheme I-55); 4-chloro-2-(2-chloro-benzyloxy)-N-(pyrid-3-yl) benzamide (Scheme I-56); 2-(2-chloro-benzyloxy)-5-nitro-N-(pyridin-3-yl) benzamide (Scheme I-57); 4-bromo-2-(2-chloro-benzyloxy)-N-(pyridin-3-yl) benzamide (Scheme I-58); 2-(2-chloro-benzyloxy)-5-methoxy-N-(pyridin-3-yl) benzamide (Scheme I-59); 2-(2-chloro-benzyloxy)-4-methoxy-N-(pyridin-3-yl) benzamide (Scheme I-60).

The structures were confirmed correct and data are as follow:

Scheme I-54 m.p 129.2-131.9° C. MS(ESI) (m/z): 407.0 $(M+H)^+$. $^1H$ NMR (400 MHz, DMSO-$d_6$) δ ppm 10.27 (s, 1H), 8.54 (d, J=2.3 Hz, 1H), 8.24 (dd, J=4.6, 1.2 Hz, 1H), 7.99 (d, J=8.3 Hz, 1H), 7.64 (d, J=2.6 Hz, 1H), 7.61 (dd, J=8.7, 2.7 Hz, 1H), 7.53-7.40 (m, 4H), 7.31 (dd, J=8.3, 4.7 Hz, 1H), 5.37 (s, 2H).

Scheme I-55 m.p 153.3-154.7° C. MS(ESI) (m/z): 391.0 $(M+H)^+$. $^1H$ NMR (400 MHz, DMSO-$d_6$) δ ppm 10.51 (s, 1H), 8.75 (d, J=1.4 Hz, 1H), 8.29 (d, J=4.2 Hz, 1H), 8.11 (d, J=8.3 Hz, 1H), 7.65 (d, J=2.5 Hz, 1H), 7.57 (dd, J=8.8, 2.6 Hz, 1H), 7.52 (dd, J=8.8, 5.1 Hz, 1H), 7.45 (dd, J=9.4, 2.9 Hz, 1H), 7.36 (dd, J=8.3, 4.8 Hz, 1H), 7.32 (d, J=8.9 Hz, 1H), 7.21 (td, J=8.5, 3.0 Hz, 1H), 5.27 (s, 2H).

Scheme I-56 m.p 117.6-121.7° C. MS(ESI) (m/z): 373.0 $(M+H)^+$. $^1H$ NMR (400 MHz, DMSO-$d_6$) δ ppm 10.32 (s, 1H), 8.62 (d, J=2.3 Hz, 1H), 8.26 (dd, J=4.6, 1.1 Hz, 1H), 8.06 (d, J=8.4 Hz, 1H), 7.68 (d, J=8.2 Hz, 1H), 7.65 (d, J=7.7 Hz, 1H), 7.49 (d, J=7.9 Hz, 1H), 7.47 (d, J=1.5 Hz, 1H), 7.40-7.27 (m, 3H), 7.19 (dd, J=8.2, 1.5 Hz, 1H), 5.34 (s, 2H).

Scheme I-57 m.p 175.7-177.9° C. MS(ESI) (m/z): 384.0 $(M+H)^+$. $^1H$ NMR (400 MHz, DMSO-$d_6$) δ ppm 10.56 (s, 1H), 8.69 (d, J=2.3 Hz, 1H), 8.46 (d, J=2.9 Hz, 1H), 8.42 (dd, J=9.1, 2.9 Hz, 1H), 8.31-8.27 (m, 1H), 8.08 (d, J=8.4 Hz, 1H), 7.67-7.61 (m, 1H), 7.55 (d, J=9.2 Hz, 1H), 7.50 (d, J=7.9 Hz, 1H), 7.37 (dd, J=7.8, 5.6 Hz, 2H), 7.31 (t, J=7.4 Hz, 1H), 5.45 (s, 2H).

Scheme I-58 m.p 117.6-120.1° C. MS(ESI) (m/z): 417.0 $(M+H)^+$. $^1H$ NMR (400 MHz, DMSO-$d_6$) δ ppm 10.32 (s, 1H), 8.62 (d, J=2.3 Hz, 1H), 8.26 (dd, J=4.7, 1.4 Hz, 1H), 8.05 (ddd, J=8.3, 2.3, 1.5 Hz, 1H), 7.64 (dd, J=7.6, 1.5 Hz, 1H), 7.59 (t, J=5.2 Hz, 2H), 7.49 (dd, J=7.9, 1.1 Hz, 1H), 7.34 (qdd, J=15.9, 7.5, 1.4 Hz, 4H), 5.33 (s, 2H).

Scheme I-59 m.p 97.3-99.8° C. MS(ESI) (m/z): 369.0 $(M+H)^+$. $^1H$ NMR (400 MHz, DMSO-$d_6$) δ ppm 10.36 (s, 1H), 8.64 (d, J=2.3 Hz, 1H), 8.29-8.23 (m, 1H), 8.07 (d, J=8.5 Hz, 1H), 7.63 (d, J=6.4 Hz, 1H), 7.48 (d, J=7.9 Hz, 1H), 7.39-7.22 (m, 5H), 7.10 (dd, J=9.0, 3.1 Hz, 1H), 5.25 (s, 2H), 3.75 (s, 3H).

Scheme I-60 m.p 122.1-124.4° C. MS(ESI) (m/z): 369.0 $(M+H)^+$. $^1H$ NMR (400 MHz, DMSO-$d_6$) δ ppm 10.05 (s, 1H), 8.46 (d, J=2.3 Hz, 1H), 8.23 (dd, J=4.7, 1.3 Hz, 1H), 8.01 (d, J=8.4 Hz, 1H), 7.82-7.76 (m, 1H), 7.71 (dd, J=7.4, 1.3 Hz, 1H), 7.53 (dd, J=7.9, 1.0 Hz, 1H), 7.41 (td, J=7.7, 1.7 Hz, 1H), 7.35 (td, J=7.5, 1.1 Hz, 1H), 7.30 (dd, J=8.3, 4.7 Hz, 1H), 6.86 (d, J=2.1 Hz, 1H), 6.71 (dd, J=8.7, 2.2 Hz, 1H), 5.37 (s, 2H), 3.84 (s, 3H).

Application Case 11: Synthesis of Scheme I-16, I-21, I-24, I-27, I-29, I-32, I-33, I-34, I-36, I-39, I-40 and I-43 Hydrochlorides 1. Synthesis of Scheme I-24 Hydrochloride 0.33 g (1.0 mmol, 1.0 eq) scheme I-24 was dissolved in 10 ml anhydrous EA. To the solution 1.2 ml EA solution (c=1.25 mol/L) of HCl (g, 1.5 mmol, 1.5 eq) was added dropwise under the condition of ice water bath. After 10 minutes, the reaction mixture was desolventized by vacuum distillation and 0.24 g white powdery solid was obtained, yield 64.9%. Scheme I-24 hydrochloride m.p 154.4-157.2° C.

2. Synthesis of Scheme I-27 Hydrochloride 0.42 g (1.26 mmol, 1.0 eq) scheme I-27 was dissolved in 13 ml anhydrous EA. To it 1.5 ml EA solution (c=1.25 mol/L) of HCl (g, 1.75 mmol, 1.5 eq) was added dropwise under the condition of ice water bath. After 10 minutes, the reaction mixture was desolventized by vacuum distillation and 0.33 g white powdery solid was obtained, yield 70.8%. Scheme I-27 hydrochloride m.p 158.0-161.3° C.

3. Synthesis of Scheme I-40 Hydrochloride 0.23 g (0.5 mmol, 1.0 eq) scheme I-40 was dissolved in 5 ml anhydrous EA. To it 0.6 ml EA solution (c=1.25 mol/L) of HCl (g, 0.75 mmol, 1.5 eq) was added dropwise under the condition of ice water bath. After 10 minutes, the reaction mixture was desolventized by vacuum distillation and 0.16 g white powdery solid was obtained, yield 64.0%. Scheme I-40 hydrochloride m.p 156.9-159.2° C.

Hydrochlorides of scheme I-16, I-21, I-29, I-32, I-33, I-34, I-36, I-39, and I-43 were obtained through method mentioned above.

Application Case 12: Determination of In Vitro Inhibition of 2-Alkoxy-Benzoyl Aromatic Amines to Sphingomyelin Synthase 2

Laboratory Instruments and Materials
1. Electric-heated thermostatic water bath (Shanghai Hengyi Science and Technology Co., Ltd.)
2. Vortex Mixers (XW-80A, Shanghai Jingke Industrial Co., Ltd.)
3. High-speed centrifuge (Eppendorf 5804R)
4. HPLC Agilent 1100 (Agilent Technologies, Palo Alto, Calif., USA), equipped with a quaternary pump, a vacuum degassing and an FLD fluorescence detector.
5. HPLC Column: Agilent C18 RP (250 mm×4.6 mm 5 μm)
6. DMPC. Purchased from Santa Cruz (USA) and dissolved in ethanol to prepare a solution of 40 mM.
7. C6-NBD-Ceramide (6-((N-(7-nitrobenz-2-oxa-1,3-diazol-4-yl)amino)hexanoyl)-sphingosine). Purchased from Santa Cruz (USA) and dissolved in ethanol to prepare a solution of 1.16 mM.
8. C6-NBD-SM (N—(N-(7-nitro-2,1,3-benzoxadiazol-4-yl)-epsilon-amino hexanoyl) sphingosylphosphoryl choline). Purchased from Sigma-Aldrich (USA) and dissolved in ethanol to prepare a solution of 1 mg/mL.
9. The organic solvents were purchased from Shanghai Sinopharm Reagent Company; methanol is of HPLC grade; water is ultrapure water filtrated by Milli-Q pump and deionized and ultrafiltrated by 0.22 μm ultrafiltration membrane. Other biological supplies are purchased in domestic companies.
10. Preparation of SMS homogenate extraction buffer (Buffer1): (50 mM Tris hydrochloride, pH 7.4, 5% anhydrous sucrose, 1 mM ethylenediaminetetraacetic acid) 1.2114 g tris(hydroxymethyl)aminomethane hydrochloride (Tris-HCl) was dissolved in 100 ml distilled water. Then 84 ml 0.1 mol/L hydrochloric acid was added. Constant volume to 200 ml. Finally, 10 g sucrose and 58.45 mg EDTA were dissolved in the mixture.
11. Preparation of SMS test buffer (Buffer1): (100 mM Hepes, 30 mM $MnCl_2$, 3% fatty acid free BSA): 1.1916 g 4-(2-hydroxyethyl)-1-peperazineethanesulfonic acid (Hepes), 0.2969 g $MnCl_2.4H_2O$ and 0.3 g fatty acid free bovine serum albumin were dissolved in distilled water then constant volume to 50 ml.
12. Preparation of under tested compound solution: To each accurate weighed compound for 1~2 mg, an appropriate amount of DMSO was added to formulate a stock solution of 6 mM precisely. To a certain volume of the DMSO stock solution of the test compound, the appropriate volume of DMSO was added to dilute the solution to the desired concentration.
13. SMS2 high-expressed insect cell homogenate was prepared by Xu Yanhui group from Institutes of Biomedical Sciences, Fudan University.

Part 1 Activity Assay for Inhibition of 2-Alkoxy-Benzoyl Aromatic Amines to Sphingomyelin Synthase 2

250 μL tri-distilled water, 30 μL Buffer2, 4 μL SMS2 high-expressed insect cell homogenate (total protein content is 0.5 μg/μL) and 10 μL DMSO or DMSO solution of under tested compound were added to 1.5 mL eppendorf tube, vortex mixed for 30 seconds and then incubated in a 37° C. water bath for 0.5 h. 3 μL ethanol solution of DMPC (40 mM) and 3 μL ethanol solution of C6-NBD-Ceramide (1.16 mM) were added, vortex mixed for 30 seconds, and then incubate in a 37° C. water bath for 2.0 hours. To it 600 μL anhydrous ethanol was added vortex mixed for 1 minute and centrifuged 10 minutes in 10000 rpm and 600 μL supernatant was taken out and stored at 4° C. for HPLC analysis.

Using the same HPLC fluorogenic quantitative detecting method as reference (Xiaodong Deng; Hong Sun; et al. *Analytical Letters*, 2012, 45:12, 1581-1589) to analysize samples obtained above. Analysize and record peak areas of C6-NBD-SM (Asm) and C6-NBD-Ceramide (Acer) of each sample from blank group, positive control group (compound D2) and under tested compound group. The data were parallelly determined for 3 times. Calculate inhibition rate from the formula below:

$$\text{Inhibition rate \%} = \frac{\text{Blank}(Asm) - \text{Tested compound}(Asm)}{\text{Blank}(Asm)} \times 100$$

In vitro SMS2 inhibitory activity data of scheme I-1~I-60 obtained by HPLC fluorogenic quantitative detecting method are listed below:
1) the inhibition rate of 2-(2-fluoro-benzyloxy)-N-(pyridin-3-yl) benzamide (scheme I-1) at 5 μM was 53.8%;

2) the inhibition rate of 2-(3-fluoro-benzyloxy)-N-(pyridin-3-yl) benzamide (scheme I-2) at 5 μM was 69.3%;

3) the inhibition rate of 2-(3-nitro-benzyloxy)-N-(pyridin-3-yl) benzamide (scheme I-3) at 50 μM was 64.6%;

4) the inhibition rate of 2-(3-cyano-benzyloxy)-N-(pyridin-3-yl) benzamide (scheme I-4) at 50 μM was 66.0%;

5) the inhibition rate of 2-((4-methoxy) benzyloxy)-N-(pyridin-3-yl) benzamide (scheme I-5) at 50 μM was 23.0%;

6) the inhibition rate of 2-(2-cyano-benzyloxy)-N-(pyridin-3-yl) benzamide (scheme I-6) at 50 μM was 50.0%;

7) the inhibition rate of 2-(3-chloro-benzyloxy)-N-(pyridin-3-yl) benzamide (scheme I-7) at 5 μM was 70.6%;

8) the inhibition rate of 2-(3-bromo-benzyloxy)-N-(pyridin-3-yl) benzamide (scheme I-8) at 50 μM was 67.1%;

9) the inhibition rate of 2-(4-bromo-benzyloxy)-N-(pyridin-3-yl) benzamide (scheme I-9) at 50 μM was 14.7%;

10) the inhibition rate of 2-((3-methyl) benzyloxy)-N-(pyridin-3-yl) benzamide (scheme I-10) at 50 μM was 69.5%;

11) the inhibition rate of 2-((2-methyl) benzyloxy)-N-(pyridin-3-yl) benzamide (scheme I-11) at 5 μM was 71.3%;

12) the inhibition rate of 2-((2-nitro) benzyloxy)-N-(pyridin-3-yl) benzamide (scheme I-12) at 50 μM was 35.5%;

13) the inhibition rate of 2-((4-nitro) benzyloxy)-N-(pyridin-3-yl) benzamide (scheme I-13) at 50 μM was 11.8%;

14) the inhibition rate of 2-((4-methylphenyl) benzyloxy)-N-(pyridin-3-yl) benzamide (scheme I-14) at 50 μM was 69.0%;

15) the inhibition rate of 2-((4-cyanobenzyl) benzyloxy)-N-(pyridin-3-yl) benzamide (scheme I-15) at 50 μM was 15.0%;

16) the inhibition rate of 2-((2-chloro-5-fluoro) benzyloxy)-N-(pyridin-3-yl) benzamide (scheme I-16) at 5 μM was 75.7%;

17) the inhibition rate of 2-((2,6-dichlorophenyl) benzyloxy)-N-(pyridin-3-yl) benzamide (scheme I-17) at 5 μM was 77.2%;

18) the inhibition rate of 2-((2-fluoro-3-chloro) benzyloxy)-N-(pyridin-3-yl) benzamide (scheme I-18) at 5 μM was 55.2%;

19) the inhibition rate of 4-((2-(pyridin-3-ylcarbamoyl) phenoxy) methyl) benzoate (scheme I-19) at 10 μM was 2.9%;

20) the inhibition rate of 2-((4-trifluoromethyl) benzyloxy)-N-(pyridin-3-yl) benzamide (scheme I-20) at 10 μM was 3.9%;

21) the inhibition rate of 2-((5-fluoro-2-methyl) benzyloxy)-N-(pyridin-3-yl) benzamide (scheme I-21) at 10 μM was 84.7%;

22) the inhibition rate of 2-(3-((2-(pyridin-3-ylcarbamoyl) phenoxy) methyl) phenoxy) acetate (scheme I-22) at 10 μM was 15.3%;

23) the inhibition rate of 2-((3-methoxy) benzyloxy)-N-(pyridin-3-yl) benzamide (scheme I-23) at 10 μM was 59.8%;

24) the inhibition rate of 2-((2-methoxy) benzyloxy)-N-(pyridin-3-yl) benzamide (scheme I-24) at 10 μM was 89.4%;

25) the inhibition rate of 2-((2,5-dimethoxy) benzyloxy)-N-(pyridin-3-yl) benzamide (scheme I-25) at 10 μM was 78.9%;

26) the inhibition rate of 2-((2-benzyloxy) benzyloxy)-N-(pyridin-3-yl) benzamide (scheme I-26) at 10 μM was 76.9%;

27) the inhibition rate of 2-((2-ethyl) benzyloxy)-N-(pyridin-3-yl) benzamide (scheme I-27) at 5 μM was 78.4%;

28) the inhibition rate of 2-((4-ethyl) benzyloxy)-N-(pyridin-3-yl) benzamide (scheme I-28) at 10 μM was 10.1%;

29) the inhibition rate of 2-((2,6-dimethyl) benzyloxy)-N-(pyridin-3-yl) benzamide (scheme I-29) at 10 μM was 88.8%;

30) the inhibition rate of 2-((2-ethoxy) benzyloxy)-N-(pyridin-3-yl) benzamide (scheme I-30) at 10 μM was 86.3%;

31) the inhibition rate of 2-((2-methoxy-5-chloro) benzyloxy)-N-(pyridin-3-yl) benzamide (scheme I-31) at 10 μM was 92.4%;

32) the inhibition rate of 2-((2-chloro-6-fluoro) benzyloxy)-N-(pyridin-3-yl) benzamide (scheme I-32) at 10 μM was 82.3%;

33) the inhibition rate of 2-((2,5-dichloro) benzyloxy)-N-(pyridin-3-yl) benzamide (scheme I-33) at 10 μM was 87.9%;

34) the inhibition rate of 2-(2-(4-chlorobutoxy) benzyloxy)-N-(pyridin-3-yl) benzamide (scheme I-34) at 10 μM was 85.5%;

35) the inhibition rate of 2-(2-(5-chloro-pentoxy) benzyloxy)-N-(pyridin-3-yl) benzamide (scheme I-35) at 10 μM was 91.3%;

36) the inhibition rate of 2-(2-(6-Chloro-hexyloxy) benzyloxy)-N-(pyridin-3-yl) benzamide (scheme I-36) at 10 μM was 91.5%;

37) the inhibition rate of 2-((2-hexyloxy) benzyloxy)-N-(pyridin-3-yl) benzamide (scheme I-37) at 10 μM was 90.2%;

38) the inhibition rate of 2-((2-heptanone) benzyloxy)-N-(pyridin-3-yl) benzamide (scheme I-38) at 10 μM was 90.5%;

39) the inhibition rate of 2-((5-chloro-hexyloxy) benzyloxy)-N-(pyridin-3-yl) benzamide (scheme I-39) at 5 μM was 85.5%;

40) the inhibition rate of 2-((5-chloro-2-heptanone) benzyloxy)-N-(pyridin-3-yl) benzamide (scheme I-40) at 5 μM was 87.1%;

41) the inhibition rate of 2-((3-trifluoromethyl) benzyloxy)-N-(pyridin-3-yl) benzamide (scheme I-41) at 10 μM was 10.0%;

42) the inhibition rate of 2-((2-trifluoromethyl) benzyloxy)-N-(pyridin-3-yl) benzamide (scheme I-42) at 5 μM was 65.5%;

43) the inhibition rate of 2-((5-chloro-2-methyl) benzyloxy)-N-(pyridin-3-yl) benzamide (scheme I-43) at 5 μM was 74.8%;

44) the inhibition rate of 2-((3-chloro-2-methyl) benzyloxy)-N-(pyridin-3-yl) benzamide (scheme I-44) at 5 μM was 47.0%;

45) the inhibition rate of 2-((naphthalen-1-yl) methoxy)-N-(pyridin-3-yl) benzamide (scheme I-45) at 10 μM was 78.0%;

46) the inhibition rate of 4-((2-(pyridin-3-ylcarbamoyl) phenoxy) methyl) benzoic acid (scheme I-46) at 10 μM was 2.6%;

47) the inhibition rate of 2-(2-((2-(pyridin-3-ylcarbamoyl) phenoxy) methyl) phenoxy) acetic acid (scheme I-47) at 10 μM was 7.4%;

48) the inhibition rate of 2-(3-((2-(pyridin-3-ylcarbamoyl) phenoxy) methyl) phenoxy) acetic acid (scheme I-48) at 10 μM was 3.0%;

49) the inhibition rate of 2-((5-chloro-2-(3-methoxy-propoxy)) benzyloxy)-N-(pyridin-3-yl) benzamide (scheme I-49) at 10 μM was 75.3%;

50) the inhibition rate of 2-((5-chloro-2-(2-methoxy-ethoxy)) benzyloxy)-N-(pyridin-3-yl) benzamide (scheme I-50) at 10 μM was 54.2%;

51) the inhibition rate of 2-((5-chloro-2-(2-morpholino-ethoxy)) benzyloxy)-N-(pyridin-3-yl) benzamide (scheme I-51) at 10 μM was 24.9%;

52) the inhibition rate of 2-benzyloxy-N-(pyridin-2-yl) benzamide (scheme I-52) at 100 μM was 60.1%;

53) the inhibition rate of 2-benzyloxy-N-(pyrimidin-5-yl) benzamide (scheme I-53) at 10 μM was 38.4%;

54) the inhibition rate of 5-chloro-2-((2,6-dichlorophenyl) benzyloxy)-N-(pyridin-3-yl) benzamide (scheme I-54) at 10 μM was 42.3%;

55) the inhibition rate of 5-chloro-2-((2-chloro-5-fluoro) benzyloxy)-N-(pyridin-3-yl) benzamide (scheme I-55) at 10 μM was 31.7%;

56) the inhibition rate of 4-Chloro-2-(2-chloro-benzyloxy)-N-(pyridin-3-yl) benzamide (scheme I-56) at 10 μM was 20.0%;

57) the inhibition rate of 2-(2-chloro-benzyloxy)-5-nitro-N-(pyridin-3-yl) benzamide (scheme I-57) at 10 μM was 1.7%;

58) the inhibition rate of 4-bromo-2-(2-chloro-benzyloxy)-N-(pyridin-3-yl) benzamide (scheme I-58) at 10 μM was 19.4%;

59) the inhibition rate of 2-(2-chloro-benzyloxy)-5-methoxy-N-(pyridin-3-yl) benzamide (scheme I-59) at 10 μM was 7.2%;

60) the inhibition rate of 2-(2-chloro-benzyloxy)-4-methoxy-N-(pyridin-3-yl) benzamide (scheme I-60) at 10 μM was 13.3%.

Part 2. Determination of SMS2 Median Inhibitory Concentration of 2-Alkoxy Benzene Formyl Arylamines (Scheme I-1~I-60)

The DMSO stock solution of under tested compound (6 mM) was diluted stepwise into five concentration gradient. 10 μL solution of each concentration was added into the trial system to prepare samples with the method mentioned in the first step of application case 12. The Asm values of the five concentration solution of tested compound were measured, and the inhibition rate under the five concentration were calculated and fitted to obtain median inhibitory concentration ($IC_{50}$). Each compound was measured three parallel groups. SMS2 median inhibitory concentration of Scheme I-1~I-60 are listed below in Table 1:

TABLE 1

| SMS2 Median Inhibitory Concentration of Scheme I-1~I-60 | |
|---|---|
| Scheme I | $IC_{50}$ (μM) |
| D609 | 375 [a] |
| D2 | 56.2 [b] |
| I-1 | 3.5 |
| I-2 | 1.6 |
| I-3 | >50 |
| I-4 | 60.7 |
| I-5 | >100 |
| I-6 | 31.8 |
| I-7 | 1.4 |
| I-8 | >50 |
| I-9 | >100 |
| I-10 | >25 |
| I-11 | 1.5 |
| I-12 | >50 |
| I-13 | >100 |
| I-14 | >25 |
| I-15 | >100 |
| I-16 | 0.7 |

TABLE 1-continued

| SMS2 Median Inhibitory Concentration of Scheme I-1~I-60 | |
|---|---|
| Scheme I | $IC_{50}$ (μM) |
| I-17 | 0.7 |
| I-18 | 3.1 |
| I-19 | >100 |
| I-20 | >100 |
| I-21 | 0.7 |
| I-22 | >100 |
| I-23 | 5.7 |
| I-24 | 0.8 |
| I-25 | 2.8 |
| I-26 | 2.2 |
| I-27 | 0.9 |
| I-28 | >100 |
| I-29 | 0.9 |
| I-30 | 1.2 |
| I-31 | 0.7 |
| I-32 | 1.5 |
| I-33 | 1.0 |
| I-34 | 1.4 |
| I-35 | 0.7 |
| I-36 | 0.5 |
| I-37 | 0.7 |
| I-38 | 0.5 |
| I-39 | 0.5 |
| I-40 | 0.4 |
| I-41 | >100 |
| I-42 | 2.1 |
| I-43 | 1.1 |
| I-44 | 3.8 |
| I-45 | 2.6 |
| I-46 | >100 |
| I-47 | >100 |
| I-48 | >100 |
| I-49 | 4.1 |
| I-50 | 11.6 |
| I-51 | >50 |
| I-52 | 11.7 |
| I-53 | >25 |
| I-54 | >25 |
| I-55 | >25 |
| I-56 | >50 |
| I-57 | >100 |
| I-58 | >50 |
| I-59 | >100 |
| I-60 | >50 |

[a] Reference value.
[b] Experimental value.

What is claimed is:

1. An inhibitor of sphingomyelin synthase, wherein the inhibitor of sphingomyelin synthase is a 2-alkoxy benzene formyl arylamine compound represented by formula I, or a pharmaceutically acceptable salt, wherein the formula I is:

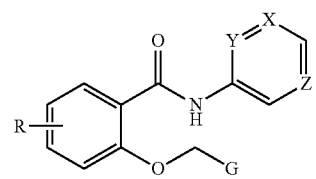

wherein,
Y is a carbon atom;
one of X and Z is a carbon atom, and the other one is a nitrogen atom;
G is selected from substituted phenyl groups and naphthyl group, wherein the substituted phenyl groups are substituted with one or two substituents selected from ortho-halogen, meta-halogen, $C_{1-7}$ alkyl, $C_{1-7}$ alkoxy and $C_{1-7}$ alkoxy substituted with halogen, phenyl or $C_{1-7}$ alkoxy; and
R is a hydrogen atom.
2. The inhibitor of sphingomyelin synthase according to claim 1, wherein the compound represented by formula I is selected from following structures:
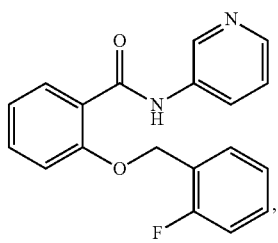
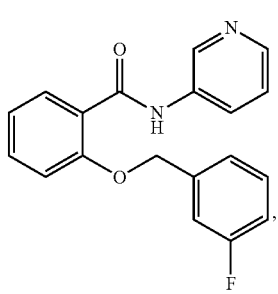
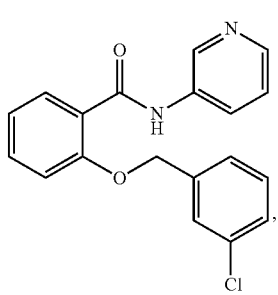
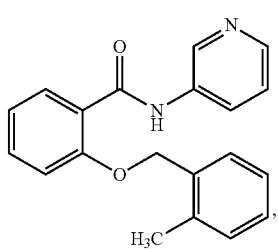
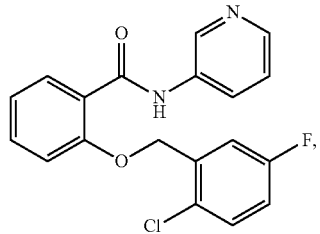
-continued
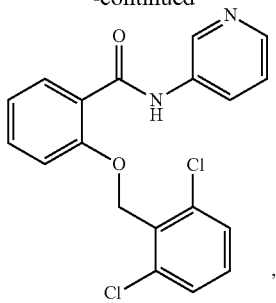
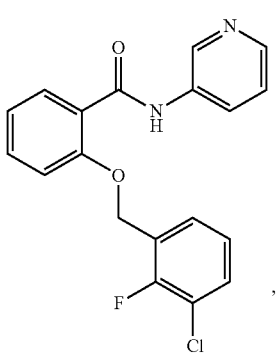
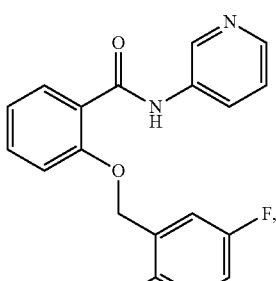
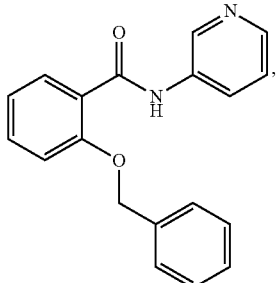
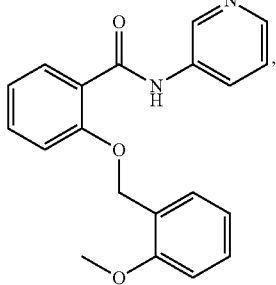

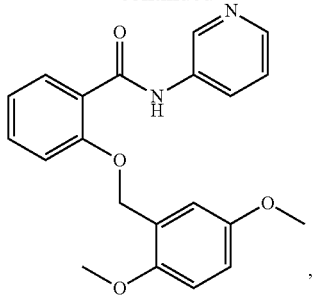
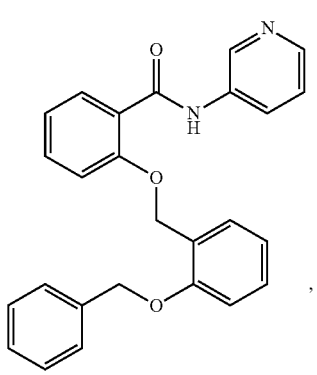
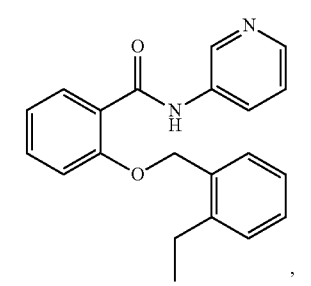
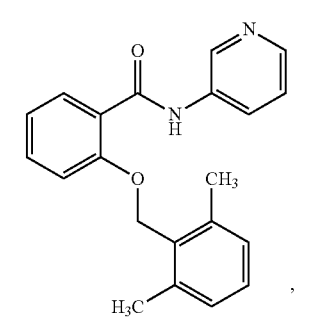
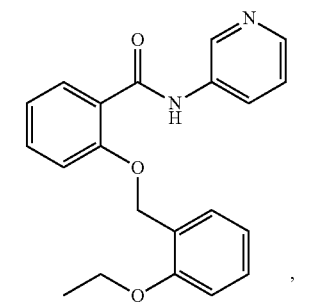
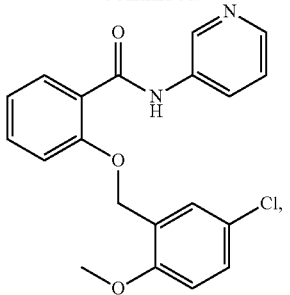
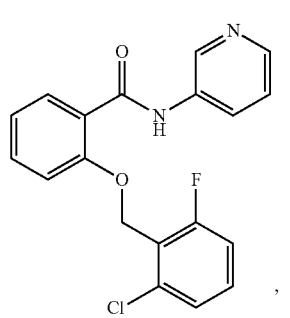
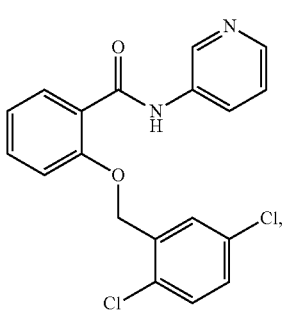
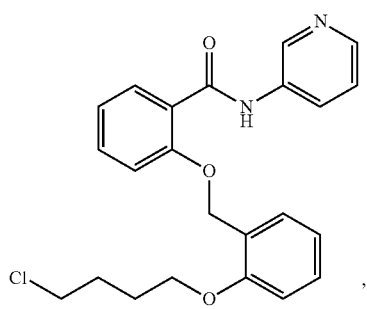
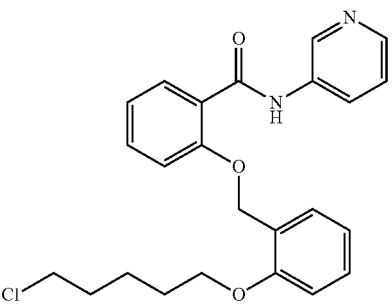

-continued

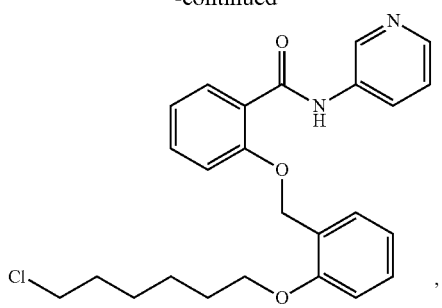

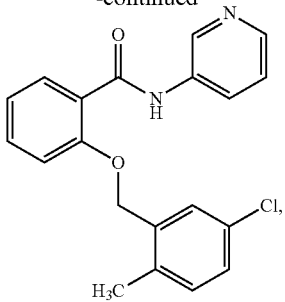

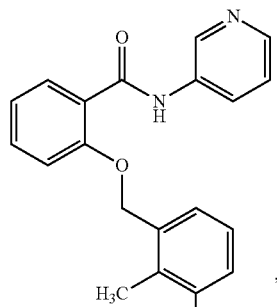

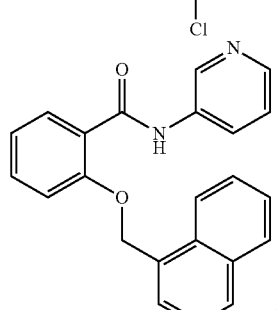

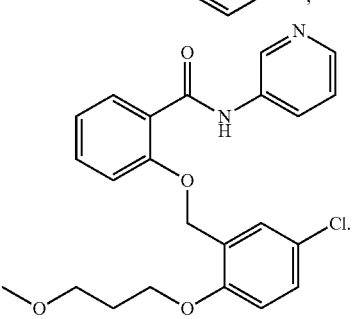

3. The inhibitor of sphingomyelin synthase according to claim 1 wherein the pharmaceutically acceptable salt is hydrochloride or hydrogen bromide salt.

4. A method of preventing or treating diseases caused by abnormal sphingomyelin increase comprising administering the 2-alkoxy benzene formyl arylamine compound represented by formula I or its pharmaceutically acceptable salts according to claim 1, wherein the diseases caused by abnormal sphingomyelin increase include atherosclerosis, fatty liver, obesity, type II diabetes, and other metabolic syndromes.

5. A pharmaceutical composition comprising the inhibitor of sphingomyelin synthase according to claim 1, and medicinally acceptable carriers.

* * * * *